United States Patent [19]

Nagyszalanczy et al.

[11] Patent Number: 6,048,363
[45] Date of Patent: Apr. 11, 2000

[54] CENTRIFUGAL BLOOD PUMP APPARATUS

[76] Inventors: Lorant Nagyszalanczy, 15004 Greenleaf St., Sherman Oaks, Calif. 91403; Kurt H. Wieland, 29811 Disney La., Vista, Calif. 92084-1225; Dan Lemay, 2514 Wilt Rd., Fallbrook, Calif. 92028; Norman E. Spicer, 77-570 Woodhaven Dr. North, Palm Desert, Calif. 92211; Jack Sternlieb, 13 Clancy La., Rancho Mirage, Calif. 92270

[21] Appl. No.: 08/854,956

[22] Filed: May 13, 1997

[51] Int. Cl.$^7$ ..................................................... A61M 1/10
[52] U.S. Cl. ........................... 623/3; 415/900; 417/423.13
[58] Field of Search ................. 623/2; 415/900, 415/115; 417/423.13, 423.11

[56] References Cited

U.S. PATENT DOCUMENTS

| | | |
|---|---|---|
| D. 273,989 | 5/1984 | Lapeyre . |
| 4,105,016 | 8/1978 | Donovan, Jr. .............................. 623/3 |
| 4,143,423 | 3/1979 | Sternlieb . |
| 4,310,930 | 1/1982 | Goldowasky . |
| 4,382,199 | 5/1983 | Isaacson . |
| 4,401,431 | 8/1983 | Arp . |
| 4,464,164 | 8/1984 | Troutner et al. . |
| 4,466,804 | 8/1984 | Hino . |
| 4,507,048 | 3/1985 | Belenger et al. . |
| 4,540,399 | 9/1985 | Litzie et al. . |
| 4,589,822 | 5/1986 | Clausen et al. . |
| 4,606,698 | 8/1986 | Clausen et al. . |
| 4,625,712 | 12/1986 | Wampler . |
| 4,636,196 | 1/1987 | Tsuji et al. . |
| 4,657,529 | 4/1987 | Prince et al. . |
| 4,661,106 | 4/1987 | Moll . |
| 4,668,459 | 5/1987 | Joh . |
| 4,753,221 | 6/1988 | Kensey et al. . |
| 4,779,614 | 10/1988 | Moise . |
| 4,780,066 | 10/1988 | Bolleter et al. . |
| 4,789,299 | 12/1988 | Demetrius et al. . |
| 4,817,586 | 4/1989 | Wampler . |
| 4,846,152 | 7/1989 | Wampler et al. . |
| 4,898,518 | 2/1990 | Hubbard et al. . |
| 4,908,012 | 3/1990 | Moise et al. . |
| 4,919,647 | 4/1990 | Nash . |
| 4,927,407 | 5/1990 | Dorman . |
| 4,932,837 | 6/1990 | Rymal . |
| 4,944,722 | 7/1990 | Carriker et al. . |
| 4,944,748 | 7/1990 | Bramm et al. . |
| 4,957,504 | 9/1990 | Chardack . |
| 4,969,865 | 11/1990 | Hwang et al. . |
| 4,981,414 | 1/1991 | Sheets . |
| 4,984,972 | 1/1991 | Clausen et al. . |
| 5,441,535 | 8/1995 | Takahashi et al. ........................... 623/3 |
| 5,443,503 | 8/1995 | Yamane ....................................... 623/3 |
| 5,531,789 | 7/1996 | Yamazaki et al. ........................... 623/3 |
| 5,776,190 | 7/1998 | Jarvik .......................................... 623/3 |

FOREIGN PATENT DOCUMENTS 9320860  10/1993  WIPO ....................................... 623/3

OTHER PUBLICATIONS

Summary Report on Hydrodynamic and Mechanical Design HDI Report R23 dated Apr. 27, 1990 by Dan B. LeMay, Lorant Nagyszalanczy and Kurt Wieland, pp. 1–12; 16 sheets of drawings.

Primary Examiner—Bruce E. Snow
Attorney, Agent, or Firm—Fulwider, Patton Lee & Utecht, LLP

[57] ABSTRACT

A centrifugal impeller-type pump for transporting blood has a new and improved design in the impeller, to allow for the elimination of stagnant flow areas, and a geometrical design that minimizes damage to the blood components. A system for controlling and stabilizing the speed of centrifugal-type pumps used in a human cardiovascular system is also provided. Further provided are methods of corrosion protection and enhancing thromboresistance, rejection of waste heat, and methods to connect the artificial heart to the cardiovascular system as a Left Ventricle Assist Device (LVAD) and as a Total Artificial Heart (TAH).

24 Claims, 18 Drawing Sheets

FIG. 7
FIG. 8
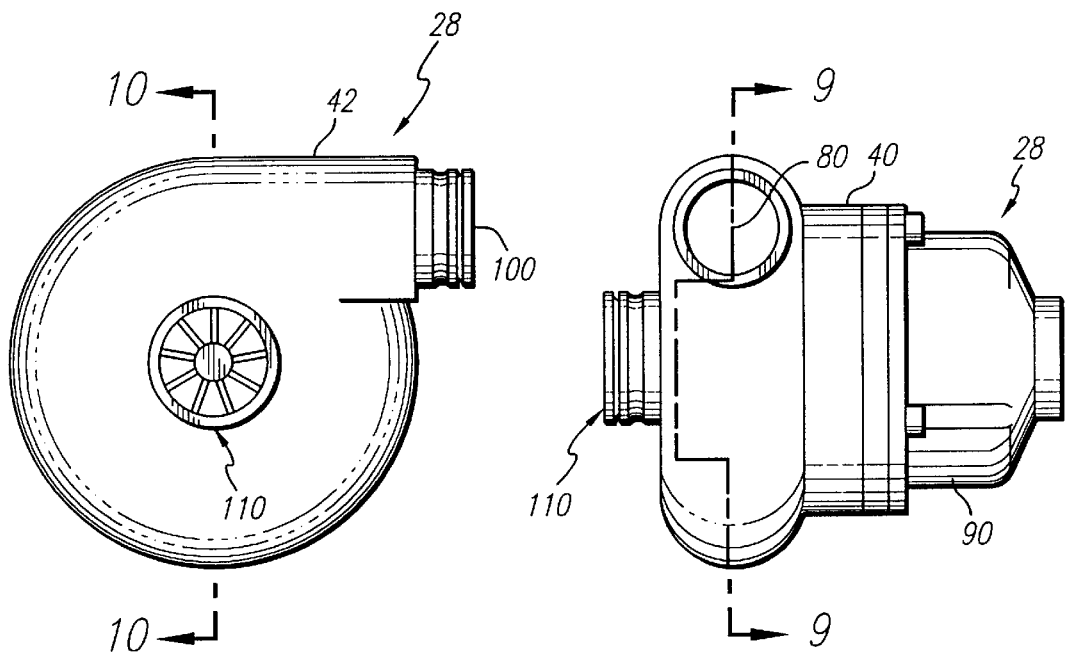
FIG. 9
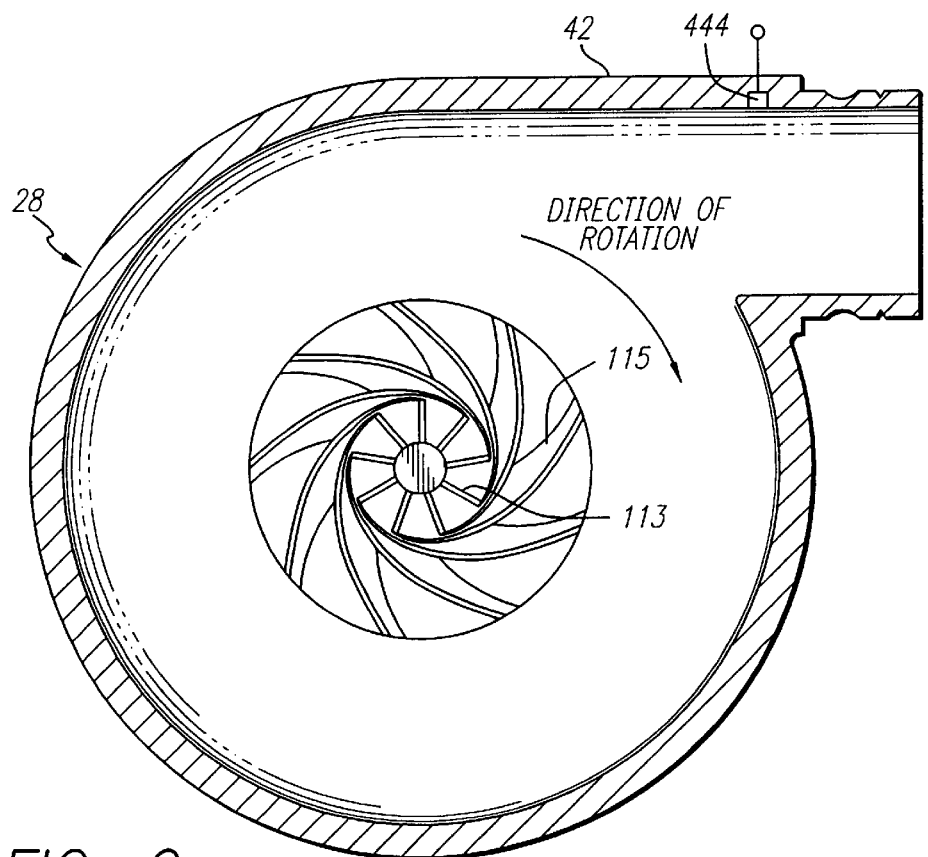

CENTRIFUGAL BLOOD PUMP APPARATUS

BACKGROUND OF THE INVENTION

1. Field of the Invention

This invention relates generally to a pump configured to transfer blood at a relatively low pressure and high volume, and, more particularly, to a pump configured to pump human blood while avoiding damage to the components of the blood, such as red corpuscles and platelets.

2. Description of Related Art

There have been various attempts to design a pump to replace the functions of the human heart. The attempts to date have been marred by a considerable number of problems, due in large part to the complicated nature of the human heart, as well as the tendency of blood components to be damaged when they come in contact with mechanical components under certain conditions of shear or stress.

While the most obvious replacement for a human heart would involve an emulation of the mechanical features of the human heart, previous attempts at such a solution have met with problems. The relatively large number of moving parts and reciprocating action of artificial hearts, such as the JARVIK heart, have contributed to mechanical complexity and unreliability and the configurations have made the creation of a small replaceable artificial heart difficult.

One alternative approach to direct emulation of the human heart has been to propose rotational pumps in order to gain the benefits of small size and mechanical simplicity. However, such pumps have demonstrated a tendency to damage the blood, resulting in fibrin accumulation and hemolysis, which makes the pumps unsuitable, particularly if a rotational pump is to be implanted as an artifical hart for long term use.

One approach chosen in the past has been to model the heart by designing a pump that mimics the kinematics of the heart, which is similar to the kinematics of a positive displacement pump. In a positive displacement pump, fluid is moved in discrete quantities, necessitating the use of some form of check valve to separate the quantities of fluid as they are moved.

While mechanical positive displacement pumps can mimic the human heart, they are by no means the ideal mechanical heart. Positive displacement pumps are typically bulky, complicated, and require artificial valves. It is also difficult to recreate the heart's reciprocating motion. In addition, there are often many hidden recesses in positive displacement pumps where blood can stagnate. Blood damage due to stagnation and turbulence also typically occurs during the beginning and the end of the strokes of fixed displacement blood pumps, as the piston or diaphragm reverses direction. Centrifugal pumps have also been designed to pump blood, and have inherent advantages over positive displacement blood pumps, but in practice have also shown a tendency to damage the blood during prolonged use.

The human heart also maintains a variable output pressure and flow schedule in the presence of a varying resistance caused by vasodilation and vasocontraction of the arteries as a result of changing demand for oxygen. In practice, this requires that a pump designed to mimic the heart have some form of feedback to control the speed of the pump and regulate the volume of fluid being pumped, so that a change in the back pressure results in a change in the speed of the pump. In the human heart, this speed control is automatically governed by the central nervous system in the form of changes to the heartbeat.

Another important factor in designing an artificial heart to pump blood is the potential for destruction of blood components when blood comes in contact with mechanical surfaces. Specifically, it is known that damage to blood components such as erythrocytes (red blood cells) and platelets in a mechanical pump is a function of the stress on the blood flow stream and the time the blood is exposed to the inside of the pump. These two factors are herein referred to as the "stress-time product." Each factor in turn depends on a number of variables, and those factors form design parameters in the design of a blood pump. Typically, stress imparted to a fluid flow stream is a function of the velocity of the surface in the pump that is driving the fluid, be it a rotor vane, piston face, or the walls of a contracting chamber. The faster the velocity of the pump driving surface, the greater the stress imparted to the fluid, and the greater the potential for surface-induced damage to the blood components. In conventional pumps, in order to slow down the velocity of the pump driving surface, without changing the amount of volume-flow that can be pumped by the pump, it is necessary to increase the area of the pump driving surface. But increasing the area also increases the size of the pump, which is a drawback to be avoided, especially if the pump is to be implanted.

The time and character of exposure of blood inside a pump as exemplified by a stress-time parameter are also critical issues in designing a heart pump. Excessive exposure time of blood to stress such as shear inside the pump can cause coagulation, emboli and fibrin accumulation, the latter manifesting itself in string-like particulate matter forming on the pump surfaces. In addition, flow separation, cavitation and swirl of blood streamlines can produce undesirable thrombus material.

The flow in a centrifugal pump, unlike the flow in a positive-displacement pump, can be continuous and non-pulsating. This results in a lower maximum velocity, and consequently the stress imparted by the pump surfaces on the blood is lower. Tests have shown that the maximum velocity in a centrifugal-type blood pump can be significantly less than the maximum velocity in a positive displacement-type blood pump. Animal tests have also shown acceptable longtime performance with steady state flow. However, some researchers feel that certain organs such as the kidneys may be affected by nonpulsing flow.

Thus, there remains a need for a compact, reliable, and simple blood pump that may be used to temporarily or permanently replace a defective human heart. It would be advantageous if such a blood pump was easy to manufacture, placed relatively little stress upon the blood components being pumped, and was easily driven by an external power source. The present invention satisfies all of these requirements.

SUMMARY OF THE INVENTION

Briefly, and in general terms, the present invention provides for an improved centrifugal blood pump apparatus that can replace some or all of the function of the human heart, either as a "bridge pump" for use from a few days to several weeks in anticipation of a heart transplant operation, a ventricular assist device (VAD) for extracorporeal use during open-heart surgery, or, with suitable control systems, as a total artificial heart (TAH). The present invention utilizes a variety of control systems to maintain a stable, dual fluid circuit, centrifugal blood pump apparatus. Employed as part of this apparatus is a new and improved centrifugal blood pump that does not suffer from many of the disadvantages of positive displacement blood pumps and conventional centrifugal pumps. The centrifugal blood pump of the invention is lightweight, small enough to be implantable, and simple in operation. The centrifugal blood pump of the invention provides for controlled flow in the presence of fluctuations in pressure, and eliminates areas of stagnant flow. The geometry of the centrifugal blood pump also minimizes the stress-time product on the blood being pumped.

In another aspect of the present invention, a blood pump apparatus is provided utilizing centrifugal pumps to serve as an artificial heart. Despite the numerous advantages a centrifugal pump has over a positive displacement pump for use as an artificial heart, some form of rotational speed control to vary the pump speed is required to maintain a variable output pressure and flow schedule in the presence of a varying resistance of the arteries. The invention accordingly provides for proper speed control of centrifugal blood pumps, so that a life support system that utilizes such pumps can maintain the proper operational characteristics required by the cardiovascular system attached to and sustained by the life support system. Thus the difficulty in maintaining a programmed flow rate in a fluid circuit, when using centrifugal pumps that experience changes in their outlet pressure, is reduced. By use of the invention, dual centrifugal pumps may be used to pump blood throughout a human cardiovascular system, and the benefits in using such centrifugal blood pumps in lieu of positive displacement pumps are realized.

In one presently preferred embodiment of the invention, a centrifugal blood pump comprises a pump enclosure having an inlet and an discharge outlet, the inlet disposed along a longitudinal axis; and an impeller surrounded by the enclosure, comprising a disc, rotatable about and radially extending from the longitudinal axis, the disc having a front face coaxial with the inlet and a back face facing away from the front face, and a plurality of blades attached to the front face of the disc. The housing comprises a stationary shroud adjacent to the blades. A primary fluid passageway is also provided between the stationary shroud and the front face of the disc and a secondary fluid passageway between the back face of the disc and the enclosure; and an opening is provided in the disc allowing fluid communication between the primary fluid passageway and the secondary fluid passageway, the opening allowing fluid to flow between the primary and secondary fluid passageways, to prevent stagnation of fluid flow.

In another preferred embodiment, the invention provides for a dual pump artificial heart blood pump apparatus for use in a mammalian cardiovascular system comprising a first pump, having an input and an output connectable to the cardiovascular system; means for sensing pressure at the output of the first pump; means for sensing pressure at the input of the first pump; and means for sensing flow rate through the first pump. A second pump is also provided, having an input and an output connectable to the cardiovascular system; means for sensing pressure at the output of the second pump; means for sensing pressure at the input of the second pump; means for sensing flow rate through the second pump; and means for controlling the speed of the first and second pumps based on the pressures and flow rates detected by the sensing means.

The present invention also provides for a method of controlling the operation of a centrifugal blood pump having an input and an output connected to a cardiovascular system, the method comprising the steps of sensing a pressure in the cardiovascular system and generating a pressure signal indicative of the pressure in the cardiovascular system; and controlling the speed of operation of the centrifugal blood pump responsive to the pressure signal. In another preferred embodiment, the invention provides for a method of controlling the operation of a centrifugal blood pump having an input and an output connected to a cardiovascular system, the method comprising the steps of sensing a blood flow rate in the cardiovascular system and generating a blood flow rate signal indicative of the blood flow rate in the cardiovascular system; and controlling the speed of operation of the centrifugal blood pump responsive to the blood flow rate signal.

Another presently preferred embodiment of the invention provides for a method of controlling dual centrifugal blood pumps operating as a heart blood pump, with a first centrifugal blood pump having an inlet connected to a cardiovascular system for receiving blood from the cardiovascular system and providing output to a respiratory system, and a second centrifugal blood pump having an inlet connected to the respiratory system to receive blood from the respiratory system and connected to deliver output to the cardiovascular system. The method comprises the steps of measuring a first pressure at the inlet of the first centrifugal blood pump and generating a first pressure signal indicative of the first pressure; controlling the speed of operation of the second centrifugal blood pump responsive to the first pressure signal; measuring a second pressure at the inlet of the second centrifugal blood pump and generating a second pressure signal indicative of the second pressure; and controlling the speed of operation of the first centrifugal blood pump responsive to the second pressure signal. Temperature and pressure sensing stations described above may be omitted or augmented and used in different sequences without violating the principles of the invention.

In yet another presently preferred embodiment, the invention provides a method of controlling the operation of a centrifugal blood pump having an input and an output connected to a cardiovascular system, the steps of the method comprising providing a pulse frequency for periodically changing blood pressure in the cardiovascular system; and controlling the speed of operation of the centrifugal blood pump responsive to the pulse frequency for periodically changing the blood pressure.

In another aspect of a presently preferred embodiment of the invention, the invention provides a system for connecting a centrifugal blood pump having an inlet and an output adapted to be connected to a mammalian cardiovascular system, comprising a flexible pump inlet cuff shaped in the form of a zone of a sphere, the inlet cuff having a surface defining a first opening and a second opening, the first opening being smaller than the second opening. Also provided are means for connecting the first opening in the inlet cuff to the inlet of the pump; means for connecting the second opening in the inlet cuff to the left atrium of a mammalian heart; and means for connecting the second opening in the inlet cuff to the right atrium of a mammalian heart.

Another presently preferred embodiment of the invention provides a method of connecting an artificial blood pump including a left ventricular blood pump and a right ventricular blood pump, the artificial blood pump having an inlet and an outlet adapted to be connected to a mammalian cardiovascular system. The method comprises separating the left ventricle from the left atrium below the aortic valve and the mitral valve; separating the right ventricle from the right atrium below the atrioventricular valve and the pulmonary valve; connecting the centrifugal blood pump and an inlet cuff with sutures to the mammalian heart; connecting an outlet of the left ventricular blood pump to biocompatible tubing and the tubing with sutures to the ascending aorta; and connecting an outlet of the right ventricular blood pump to biocompatible tubing and the tubing with sutures to the pulmonary artery.

The rotor blades of the impeller of the centrifugal pump utilized in the invention are designed to have a diameter such that their tip velocity does not create stress on the blood exceeding the maximum stress allowed by the stress-time product design parameter. Furthermore, the inlet diameter, stationary shroud, blade shroud contour, torus of the stationary shroud and the clearances between moving parts of the centrifugal pump are designed to minimize excessive stress on the blood. In addition, the geometry of the pump is such that areas in the pump that will cause stagnation, separation, or swirl of the blood streamlines, are minimized. In the present invention, the hydrodynamic efficiency of the pump is deliberately reduced in order to minimize any stagnant or recirculating flow. The invention also provides for a method of mild pulsation of blood being pumped by the centrifugal blood pump apparatus of the invention. These and other features of the present centrifugal blood pump apparatus and method of the invention are designed to minimize the stress-time product on the blood, as will be explained below.

Other features and advantages of the present invention will become apparent from the following detailed description, taken in conjunction with the accompanying drawings, which illustrate, by way of example, the principles of the invention.

BRIEF DESCRIPTION OF THE DRAWINGS

FIG. 7 is a side view of a centrifugal blood pump according to the principles of the invention.

FIG. 8 is a view looking into the outlet end of the pump of FIG. 7.

FIG. 9 is a cross-sectional view of the pump taken along section line 9—9 of FIG. 8.

DETAILED DESCRIPTION OF THE PREFERRED EMBODIMENTS

Conventional blood pump designs for replacing the functions of the mammalian heart, and particularly the human heart, have suffered from numerous problems, and particularly from the tendency to create areas of stagnation and turbulence, leading to thrombosis, fibrin accumulation, and hemolysis. In designing a blood pump apparatus to be used for replacing all or a portion of the functions of a heart, these problems are of great concern.

A characteristic of the human heart, and of any mammalian or warm-blooded heart, is that it pumps blood in two separate blood-vascular pathways or circuits. This is illustrated schematically in FIGS. 1A and 1B. One circuit connects the heart with the lungs, while the other circuit connects the heart with the rest of the body. The arteries carry oxygen rich blood from the lungs to the heart, which pumps it to the rest of the body, while the veins carry oxygen depleted blood from the body to the heart, which pumps it to the lungs. The arteries and veins are interconnected by capillaries and the flow output from the veins is the flow input to the arteries. Thus the two circuits are interrelated but physically distinct, and furthermore operate at different pressures. The body circuit operates at a higher pressure than the the circuit connected to the lungs, as illustrated in the graph in FIG. 2. To power flow through the two circuits, it is desirable that two pumps operate in tandem, at different operating pressures, but producing the same volume flow rate. Since in the human heart the two pumps are physically joined, there can be only one speed for the two pumps, and this is the pulse rate of the heart. A double-positive displacement pump operates in a manner analogous to that of the human heart, in that it can power two fluid flow circuits at the same volume flow rate, at the same speed, and this is one reason double-positive displacement pumps are used to mimic the kinematics of the human heart.

Figure 1A:
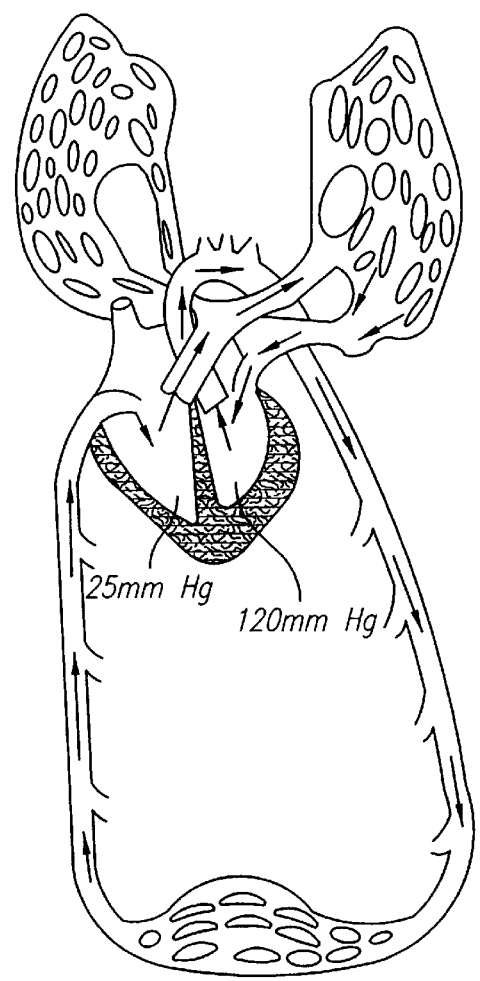
FIG. 1A schematically depicts the cardiovascular system as arranged in the human body.
Figure 1B:
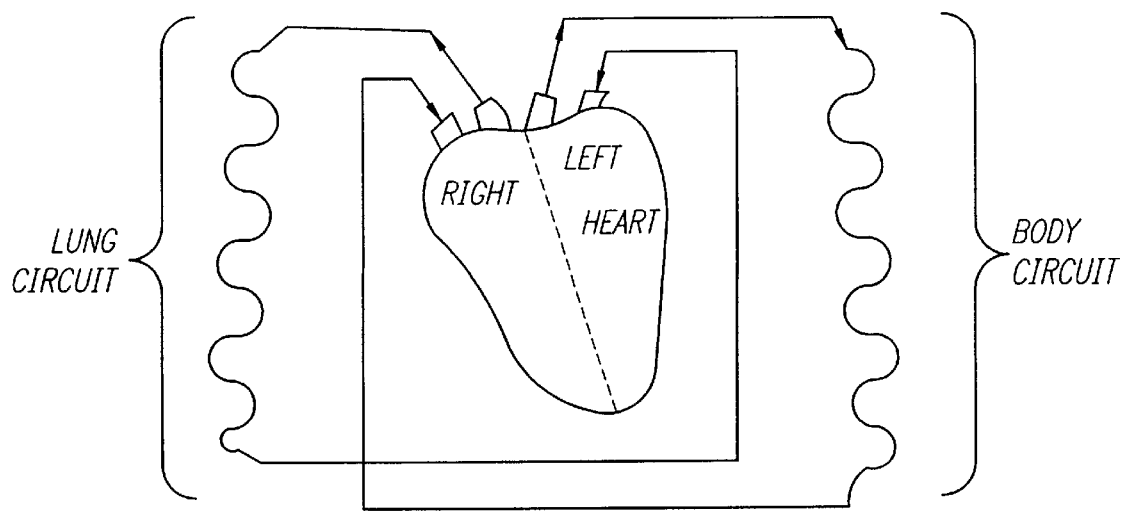
FIG. 1B is a simplified engineering schematic drawing of a human cardiovascular system.
Figure 25:
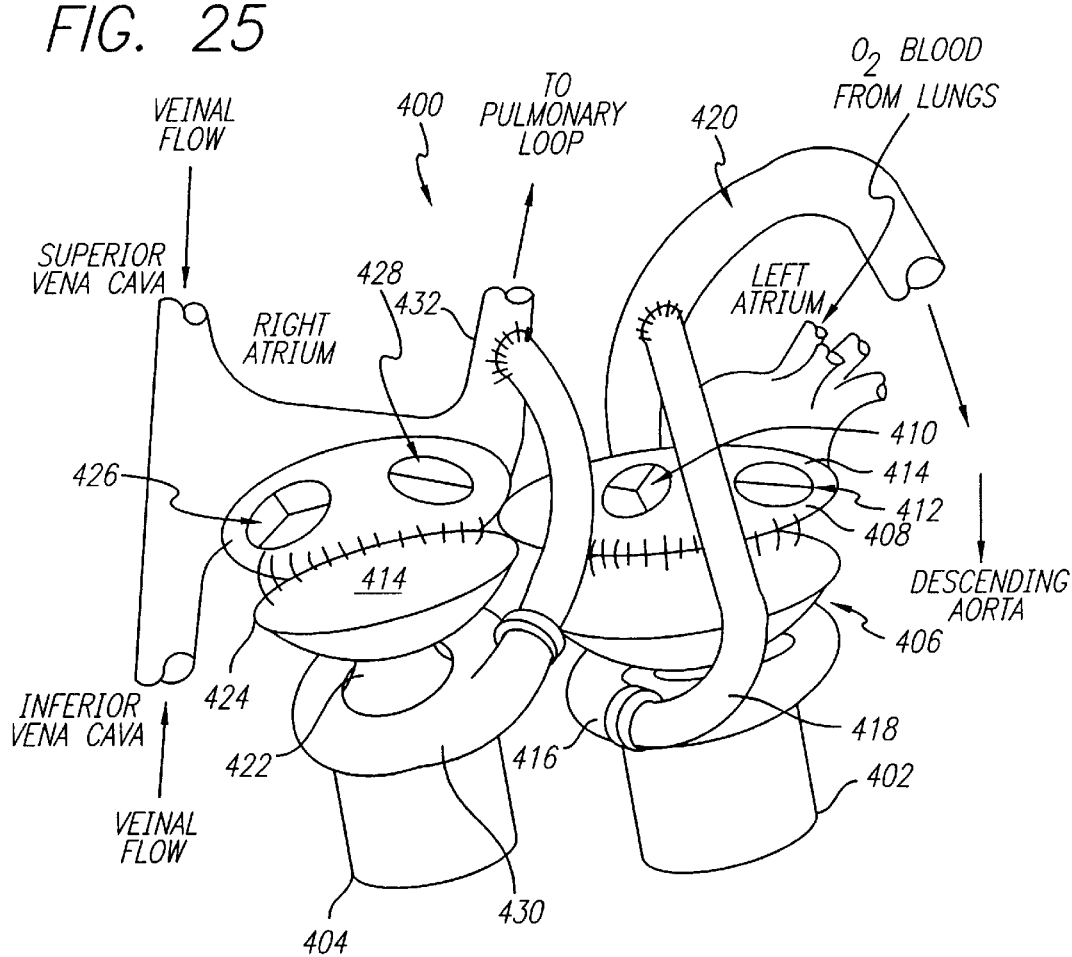
FIG. 25 illustrates the implantation of a dual blood pump Total Artificial Heart (TAH) in the human cardiovascular system, with the method shown utilizing the patient's own atrial chambers and valves.

Referring to FIG. 1A and FIG. 25, illustrating the human cardiopulmonary system, a typical cycle of the pulmonary and systemic circulation includes the following steps:

1. Blood ejected from the left ventricle during systole passes up through the aortic (tricuspid) valve. The pressure peak is approximately 120 mm Hg.
2. Blood ejected from the right ventricle during systole passes up through the pulmonary valve. The peak pressure is approximately 25 mm Hg.
3. The left ventricle ejection supplies flow to the body through the arterial vascular system via arteries, arterioles and capillaries.
4. The right ventricle ejection supplies flow to the pulmonary loop. This blood is provided by the $CO_2$ rich veinal circuit. The $CO_2$ is exchanged for $O_2$ in the lungs.
5. As diastole takes place, both veinal ($CO_2$ rich) and pulmonary ($O_2$ rich) blood flow down into the atria via the mitral and atrioventricular valves.
6. Upon depolarization of the heart, the cycle is repeated.

One problem to overcome when modeling the human heart with a pump is that while the flow in both circuits must be the same, the two circuits operate at different pressures, and yet a change in back pressure in one circuit must not disturb the volume-flow in the other circuit. In nature the problem is solved by allowing the walls of the heart to flex, so that pressure changes in one circuit will not disturb the flow in the other circuit, but in the artificial heart environment the solution is not so easily achieved. In a double-positive displacement pump, this problem is mitigated by the inherent nature of this type of pump, which has a flow output that is relatively insensitive to pressure changes. Other types of pumps, such as centrifugal pumps, require speed control to maintain a constant volume flow.

Figure 2:
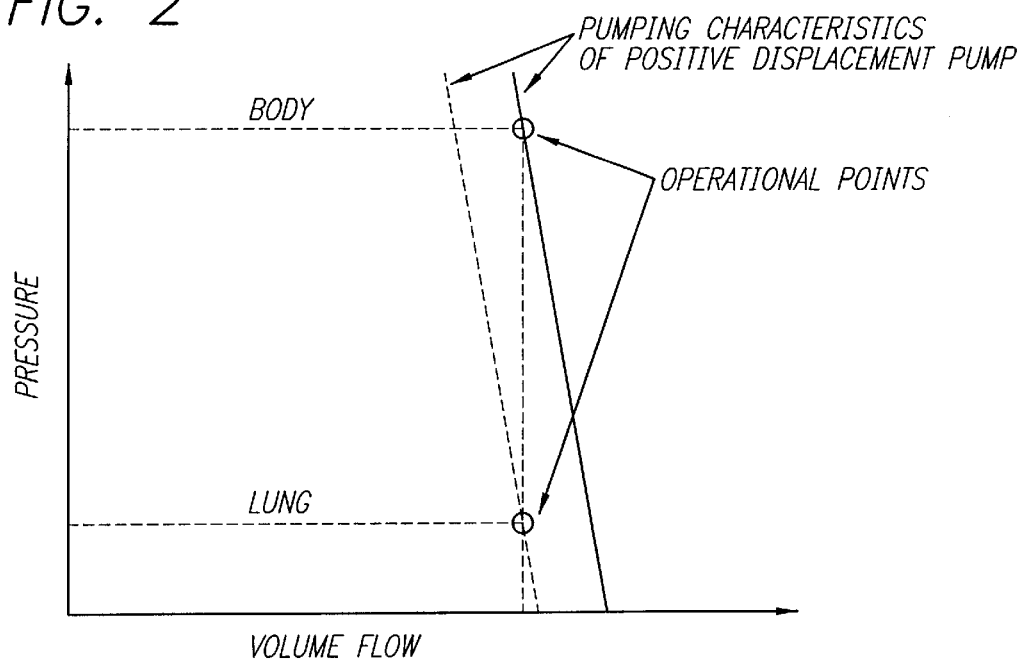
FIG. 2 is a graph showing the flow and pressure relationship of a constant speed positive displacement pump in a human cardiovascular system.
Figure 3:
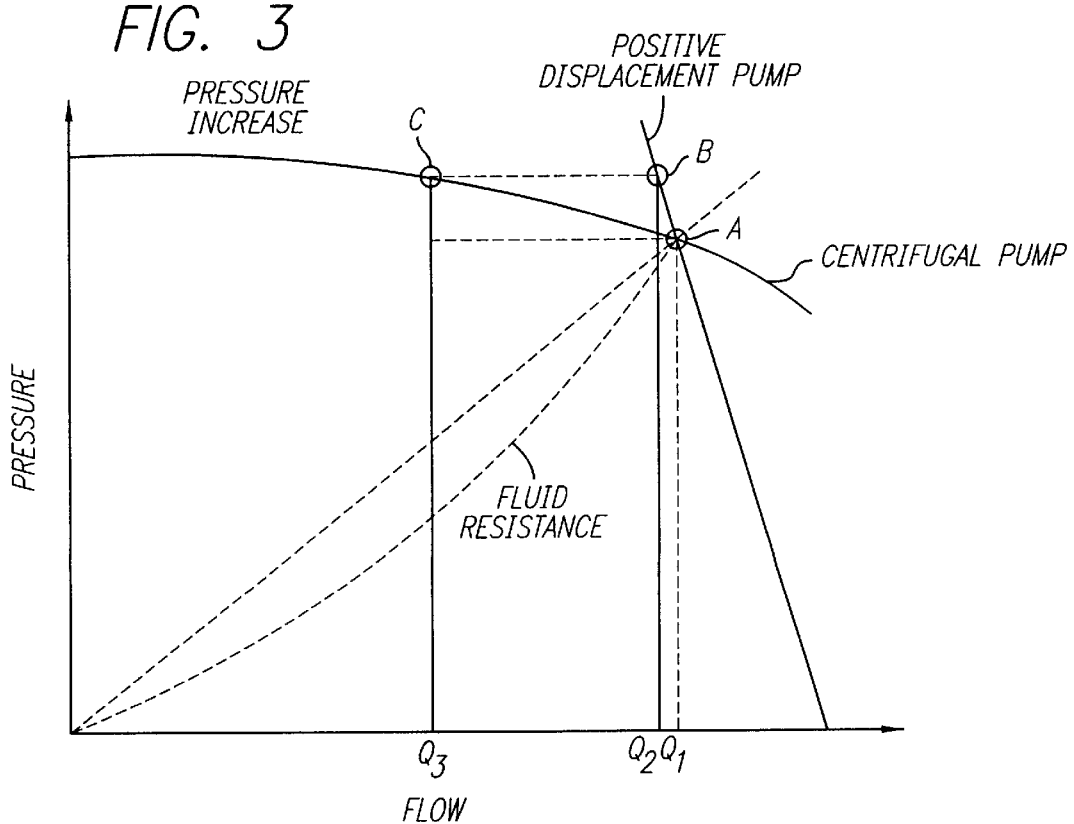
FIG. 3 is a graph illustrating the effects that a pressure increase has on two different types of pumps having constant speed.

The basic pump-flow characteristics of the positive displacement pump are represented in FIG. 2 by the downward sloping straight pressure-flow rate line. In contrast to a centrifugal pump, the relationship is linear over the operating range of the pump, so that a change in the volume flow rate gives a directly proportional change in the pressure output. The relatively steep slope of the line means that volume flow rates in positive-displacement pumps are fairly insensitive to pressure changes, as noted above, so that a relatively large change in pressure on the ordinate axis leads to a comparatively small change in volume flow rate on the abscissa axis. By contrast, the pump-flow characteristic of a centrifugal pump, as shown by the curved pressure-flow rate line of FIG. 3, is radically different than that of the positive-displacement pump. Centrifugal pumps have a non-linear relationship between pressure and flow rates, and furthermore exhibit a large change in flow rates for a given pressure change, when compared to positive-displacement pumps. This last point is illustrated in FIG. 3 by the change in volume flow rates for the two types of pumps when the inlet pressure on the pump is changed. In the positive displacement pump the volume flow rate changes from point Q1 to Q2 for a given change in pressure, while in the centrifugal pump the volume flow rate changes a larger amount, from point Q1 to Q3. To reestablish the same flow rate after such a change, the speed of the pump has to be increased.

The problems associated in maintaining constant volume flow with changes in pressure for different types of pumps can be graphically illustrated. Referring to FIG. 3, the fluid operational point or design point of a positive displacement pump and a centrifugal pump are shown at point A. This point defines the flow rate at which a pump must operate in order to adequately service a fluid circuit it is driving, and is defined by the intersection of the line representing pump-flow characteristics of the pump (in solid lines) with the line representing circuit resistance of the fluid circuit attached to the pump (in dashed lines). The pump-flow characteristic line gives the relationship between the outlet (discharge) pressure and the volume flow rate, at a given inlet pressure to the pump. A change in inlet pressure will result in a different, shifted pump-flow characteristic line. Such a change can occur in the human heart when the heart responds to an increased demand for blood flow by the body. The circuit resistance line represents the relationship between the pressure applied to the circuit and the volume flow rate possible in the circuit at this pressure. The line is non-linear due to the effects of friction and other forms of resistance to fluid flow. Increasing the resistance in a fluid circuit, as occurs in the cardiovascular system when arteries are constricted, will decrease the flow that can be accommodated, and the circuit resistance line is shifted to the left as is illustrated in FIGS. 5 and 6.

Figure 4:
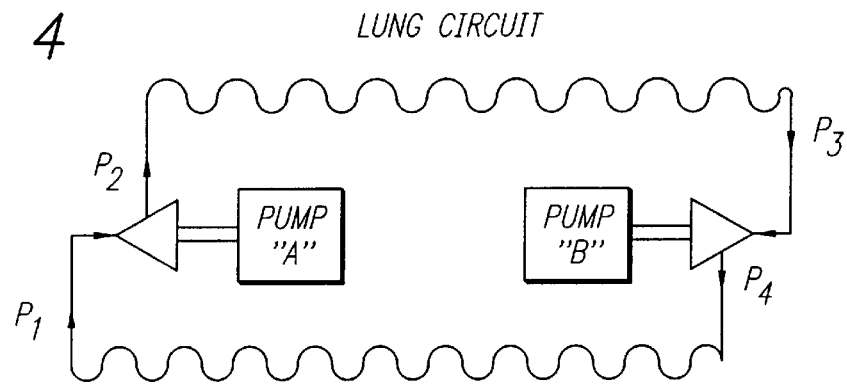
FIG. 4 is a schematic drawing of a centrifugal heart pump system, without illustration of speed control, for simplicity.
Figure 5:
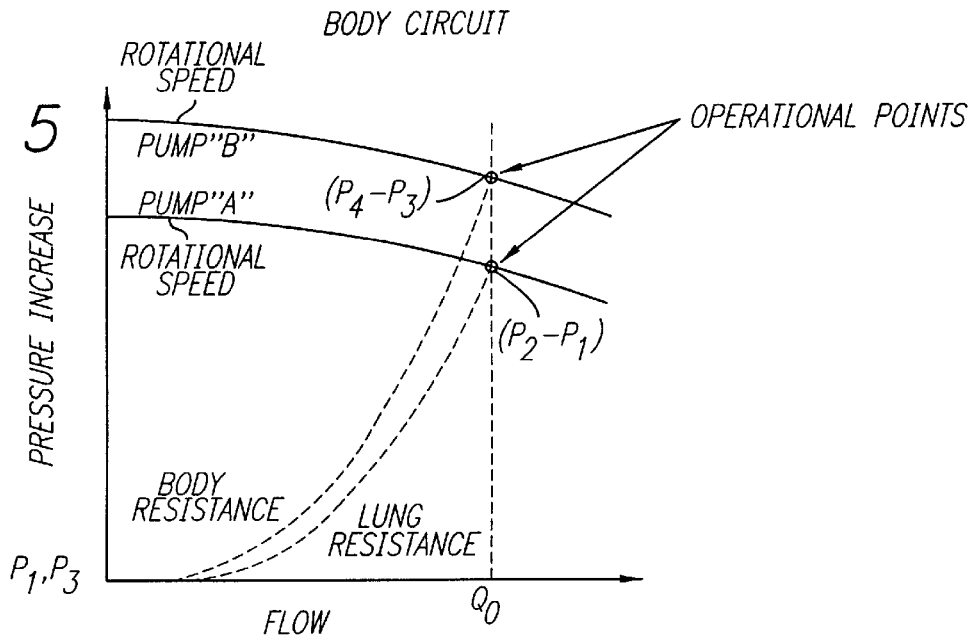
FIG. 5 is a graph showing the operational points of a human cardiovascular system controlled by the centrifugal pump system of FIG. 4 with constant rotational speed, before a change in the circuit resistance and constant flow rate of the cardiovascular system.
Figure 6:
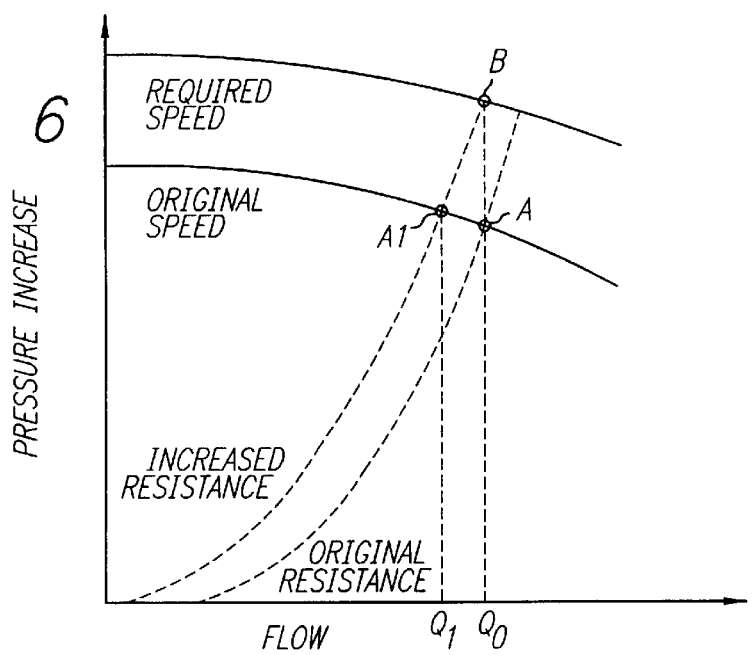
FIG. 6 is a graph similar to that of FIG. 5. showing the operational points of a human cardiovascular system controlled by the centrifugal pump system of FIG. 4 with variable rotational speed, after a change in the circuit resistance and flow rate of the cardiovascular system.

The effects of pressure, flow rate, pump speed and circuit resistance on the operational points or design points of a fluid circuit such as the one illustrated in FIG. 4 are illustrated in FIGS. 5 and 6, where an increased resistance in the circuit resistance line has the effect of changing the operational point or design point of the centrifugal pump from A to A1. Consequently, the flow rate drops from point Q0 to Q1. In order to reestablish the volume flow rate Q0, the speed of the pump has to be increased from the original speed to a required speed which gives the pump-flow characteristic curve that intersects the increased resistance line at point B.

The present invention accordingly provides for a novel design for a centrifugal blood pump which reduces the probability of damage to blood components, hemolysis and fibrin buildup within the cardiovascular system. In one preferred aspect of the invention, means are provided to control the output of the pump in order to allow the pump to respond to changing demands of the cardiovascular system.

Referring now to the drawings, and particularly to FIGS. 7 to 11, in a first preferred embodiment of the present invention, a centrifugal blood pump 28 comprises an impeller or blade shroud contour 30 coaxial and a bell-shaped portion of the stationary shroud 35. The stationary shroud, together with the housing half 40, form the outer encasement or enclosure of the pump. In a preferred embodiment, the enclosure of the pump also can comprise a collection shroud 42, for collecting the blood discharged from the impeller blades. The collection shroud preferably has a cross-sectional area substantially equal to the cross-sectional area of the discharge outlet 100. The collection shroud can also have a substantially toroidal shape. In a preferred embodiment, the collection shroud is also continuous and can be integral with the stationary shroud. Both the stationary shroud and collection shroud can be made of a plastic material, or titanium steel, for example. The impeller is comprised of a hub 45, curved rotor blades 50 and a disc 55, which form the blade hub contour 30. The disc 55 has a continuous slot 60 in its face, near the hub, with the blades 50 spanning the slot to connect the disc to the hub. The hub extends in the longitudinal axial direction, along hub drive shaft 63. The disc is attached to the rotor blades 50 at the distal edge of the blades, which is the edge of the blades furthest from the leading edge 32 of the blades, which are adjacent to the stationary shroud 35.

Input power to the impeller is supplied by way of the hub drive shaft which is connected to the impeller through splined or threaded portion 70. A spacer or seal rotor 75 can be placed on the shaft, while O-ring or comparable seals 80 prevent blood from escaping from the working chamber where blood is present into the portion of motor housing 90 encasing the pump motor.

A shaft seal is utilized to separate the blood in passages of the centrifugal blood pump from the motor and bearing cavity to avoid fibrin formation and excessive friction losses. The arrangement of the seal within the blood pump and the selection of the materials for the seal rotor and stator are significant for compatibility of the centrifugal blood pump with the biological environment.

The shaft seal is preferably a face seal that restricts contact of the pump rotor with blood to the area bounded by the recirculation slot 107 and 60, the pump blades 50, the outside of hub surfaces 45, 75 and 30 and also the inside of the torus 120, thereby leaving the cavity in the motor housing free of blood.

Figure 10:
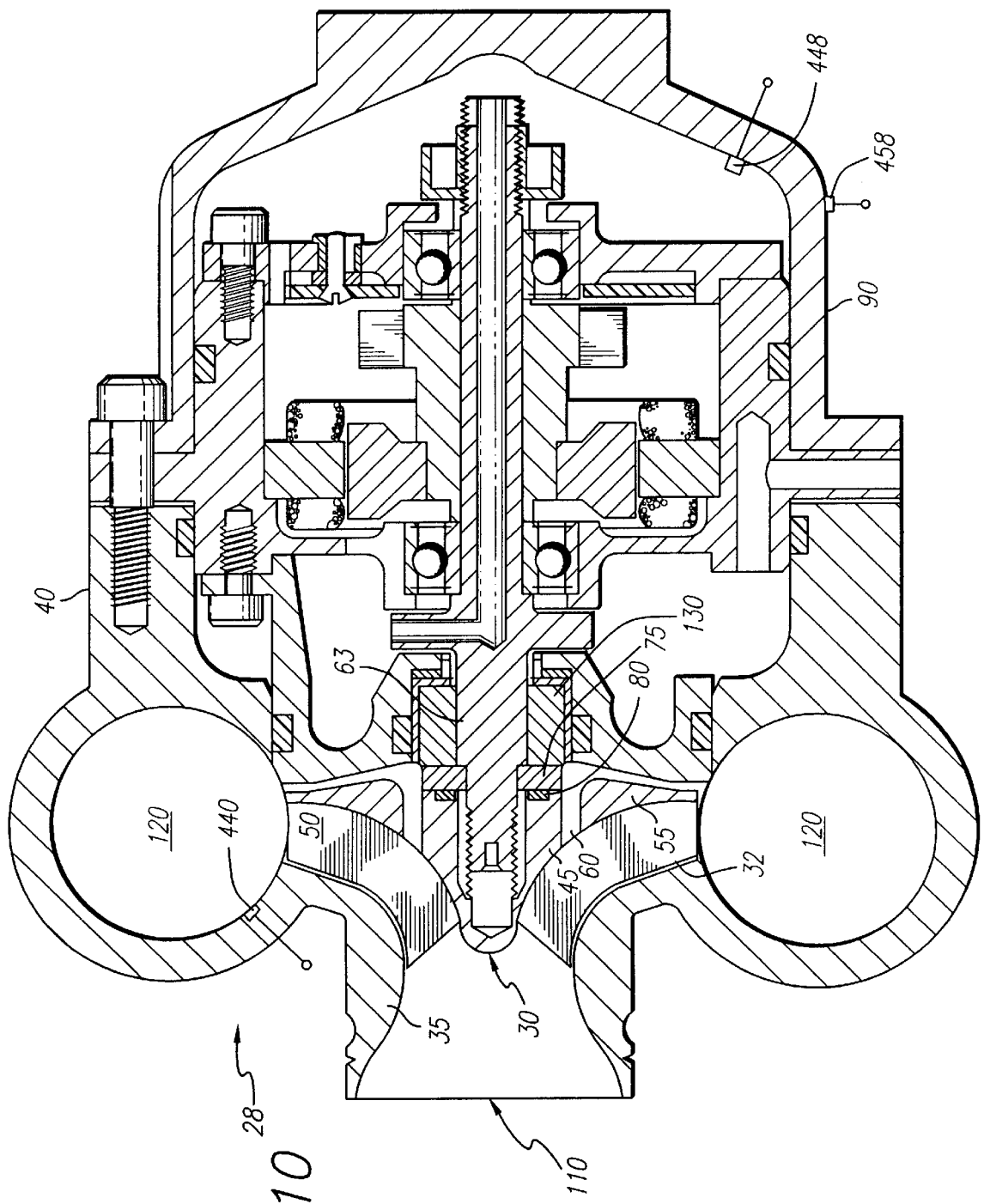
FIG. 10 is a cross-sectional view of the pump taken along section line 10—10 of FIG. 7.

The face seal preferably comprises a seal rotor 75 and a seal stator 130 having ancillary seal preloaded spring and seal housing as is illustrated in FIG. 10. This type of shaft seal has demonstrated satisfactory operation in commercial applications with various fluids. One preferred type of face seal that has proven to be most reliable is a face seal with the seal rotor 75 made from nitrided titanium and the seal stator 130 contact surface made from a specialty grade carbon ring, and with alternate stators being made from polytetrafluoroethylene (PTFE). Alternatively, the seal stator can consist of ceramic or ceramic impregnated with PTFE or a similar polymer.

The pump motor itself can be a permanent-magnet motor. Permanent-magnet motors are advantageous, since they have a very wide control range, they lack brushes and slip rings, and their use eliminates a need for a separate tachometer to measure pump speed, because they are synchronous with the pump.

The space between the stationary shroud 35 and the impeller 30 forms the working chamber of the pump, where blood is pumped from the inlet 110 to a higher pressure at the discharge outlet 100, shown in FIG. 7. The working chamber is divided into a primary fluid passageway, shown at 105 in FIG. 11, defined by the space between the stationary shroud 35 and the rotor blades 50 on the front face of the impeller disc 55, through which the majority of the blood flows, and a secondary recirculation fluid passageway 107, where some of the blood is recirculated against the main flow of blood to prevent stagnation, as will be explained below.

The blades of the impeller curve radially outward in a substantially hyperbolic or parabolic spiral. As can be seen in the cross-sectional view of FIG. 9, taken across the longitudinal axis of the pump, the blades follow a substantially logarithmic spiral when the peripheral portion of each blade is projected onto a two-dimensional plane. The impeller blades form at their inlet edges 113 an impeller inlet portion 115. At inlet portion 115 the blade ends overlap with respect to neighboring blade ends, to present an unbroken extent of blade surface area to oncoming fluid streamlines. This overlap can be most clearly seen in FIG. 9. The overlapping blades at the impeller inlet portion substantially span the diameter of the inlet opening 110 of the stationary shroud 35, and conform to the inlet bell portion of the stationary shroud, with a small clearance 118 between the blades and the stationary shroud. This clearance can be made larger than the most hydrodynamically efficient clearance, in order to decrease the stress imparted to the blood that flows in the clearance and consequently prevent surface or shear induced damage to the blood components. The stationary shroud is also made to be of a continuous shape, to avoid sudden discontinuities that might cause separation or additional stress on the blood. In addition, the inlet bell portion of the stationary shroud 35 is designed to minimize the stress-time product by being of a shape that promotes constant acceleration. Indeed, the contour of the stationary shroud is such that the shroud conforms to the outermost radial portions of the curvilinear blades. The blades form an envelope whose longitudinal cross-section profile is a generally hyperbolic or parabolic function, as can be seen in FIG. 9.

To further reduce stress on the incoming blood flow, the inlet blades have a streamlined elliptic longitudinal cross section at their leading edges, the leading edge being three-dimensional and dulled, to prevent excessive stress being generated on the incoming blood. Both of these modifications to the rotor blades decrease the stress-time product on the blood, preventing damage to the blood, at the expense of reducing the maximum hydrodynamic efficiency of the pump. To further reduce damage to the blood, the essentially parabolic shape of the impeller blades is gradually changed from inlet to discharge. Furthermore, the inlet diameter of the impeller is chosen to provide a low relative velocity of the incoming blood with respect to the blades of the impeller.

Although any suitable material can be used to form the housing, shrouds and impeller of the centrifugal blood pump, an engineering plastic material that is medically suited for use in a human body is preferred. In addition, the stationary shroud and collection shroud can be formed of a one-piece construction. The pump can be made to be disposable, but the pump may also be made suitably small enough to be implantable inside the human body. The face seal or seal stator 130 in the pump shown in FIG. 10 can preferably be made from carbon or other suitable material, to give a compact configuration that exposes no stagnant cavities to the blood flow.

At the impeller inlet portion 30, the incoming blood flow is diverted by the impeller rotor blades 50, and the blood follows the fluid streamlines bounded by the spiralling blades. The blood flow exits from the impeller rotor blades 50 tangential to the incoming axial flow, and out of the plane of the paper in the cross-sectional views shown in FIGS. 10 and 11. The blood discharged from the blades is diverted into the torus 120 of stationary shroud 35, which serves in place of the vaned diffuser or scroll of a conventional centrifugal pump design, thereby reducing the probability that the blood will be damaged by the pump. The torus is designed to have substantially the same outer diameter as the inner diameter of the outlet tubing connected to the torus, which receives the outlet flow of blood. Hence, the cross-sectional areas of the torus and discharge tubing connected to the torus are substantially equal, and there is no need for a diffuser or scroll to conduct fluid discharged from the tip of the impeller blades to the discharge tubing.

By eliminating such components as a diffuser or scroll in the instant invention, numerous advantages result. First, the stress-time product on the blood is reduced, because the relatively oversized torus allows the blood discharged from the impeller blades to exit into a larger radius of curvature than would be possible in a diffuser or scroll design. This minimizes the velocity of the blood discharged, and consequently lowers the stress exerted on the blood. Secondly, by eliminating a diffuser the unit can be shortened, and the possibility that flow will separate in a straight diffuser causing harmful thrombus production is eliminated. A torus is also simpler to manufacture, has better off-design performance than a scroll, and has a smaller incidence angle to the fluid flow than a scroll would at off design flow parameters.

While eliminating the diffuser and utilizing a torus design results in decreased hydrodynamic efficiency, it has been found that such features result in reduced damage to the blood, thereby justifying the penalty in efficiency.

Moreover, to further diminish the stress-time product on the blood, the outlet axis of the stationary shroud is made to be perpendicular to the axis of the shroud; that is, the outlet axis is non-curving.

Figure 11:
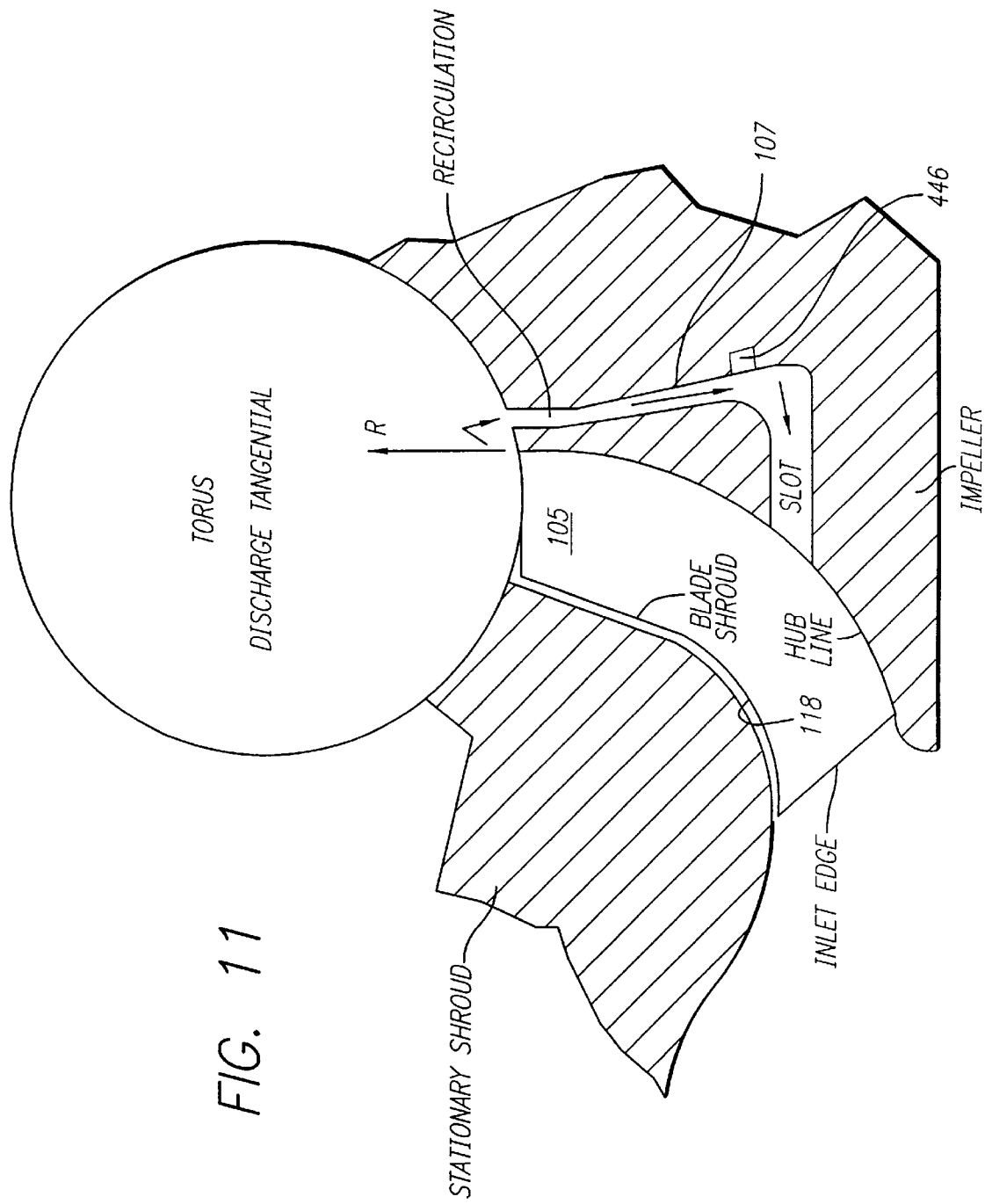
FIG. 11 is a schematic diagram illustrating the dimensions of the pump.

Another important and novel feature in the first embodiment created to decrease the stress-time product on the blood of the centrifugal type heart blood pump, is the presence of a recirculation passageway 107, shown in FIG. 11. The recirculation passageway allows blood to recirculate from the tip of the impeller blades toward the radial base of the blades, thereby avoiding blood stagnation. Specifically, the areas in the working chamber where stagnation, concomitant coagulation and fibrin accumulation of the blood could result, are located behind the back hub 45 of the impeller disc 55, near the carbon face seal 140 in FIG. 10. In the first embodiment of the centrifugal blood pump of the present invention, at least one slot 60 is provided toward the base of the impeller blades, in the impeller disc 55, through which blood can flow from behind the impeller disc to the front of the disc. Thus the slot provides for fluid communication between the primary and secondary passageways. Grooves are also present in the front face of the impeller disc, at the junction between the blades 50 and the hub 45, to prevent stagnation. In the secondary passageway 107 the blood travels along fluid streamlines that run in the opposite direction to the fluid streamlines of the primary passageway 105, with the primary passageway being the place where the majority of blood travels in when swept by the impeller rotor blades. According to one calculation, about 10% of the blood is recirculated in this manner at the design point operation of the pump, allowing the stagnant areas behind the impeller disc 55 and near the back hub to be purged of blood. The blood travels in the secondary recirculation fluid passageway counter to the main flow of blood in the primary passageway because the pressure at the tip of the impeller rotor blades is greater than the pressure at the radial base of the blades near the hub, as work is being performed on the fluid by the blades. The hydrodynamic design is made so that this will be achieved at all operational conditions. While in the preferred embodiment shown in FIG. 10 one continuous slot, surrounding the hub and shaft of the impeller as shown, it is envisioned that more than one such slot or a different configuration of opening may be provided in the impeller without departing from the scope of the invention. The invention utilizes the above recirculation feature to reduce the stress-time product on the blood, with the only penalty being a slight decrease in hydrodynamic efficiency.

Figure 18:
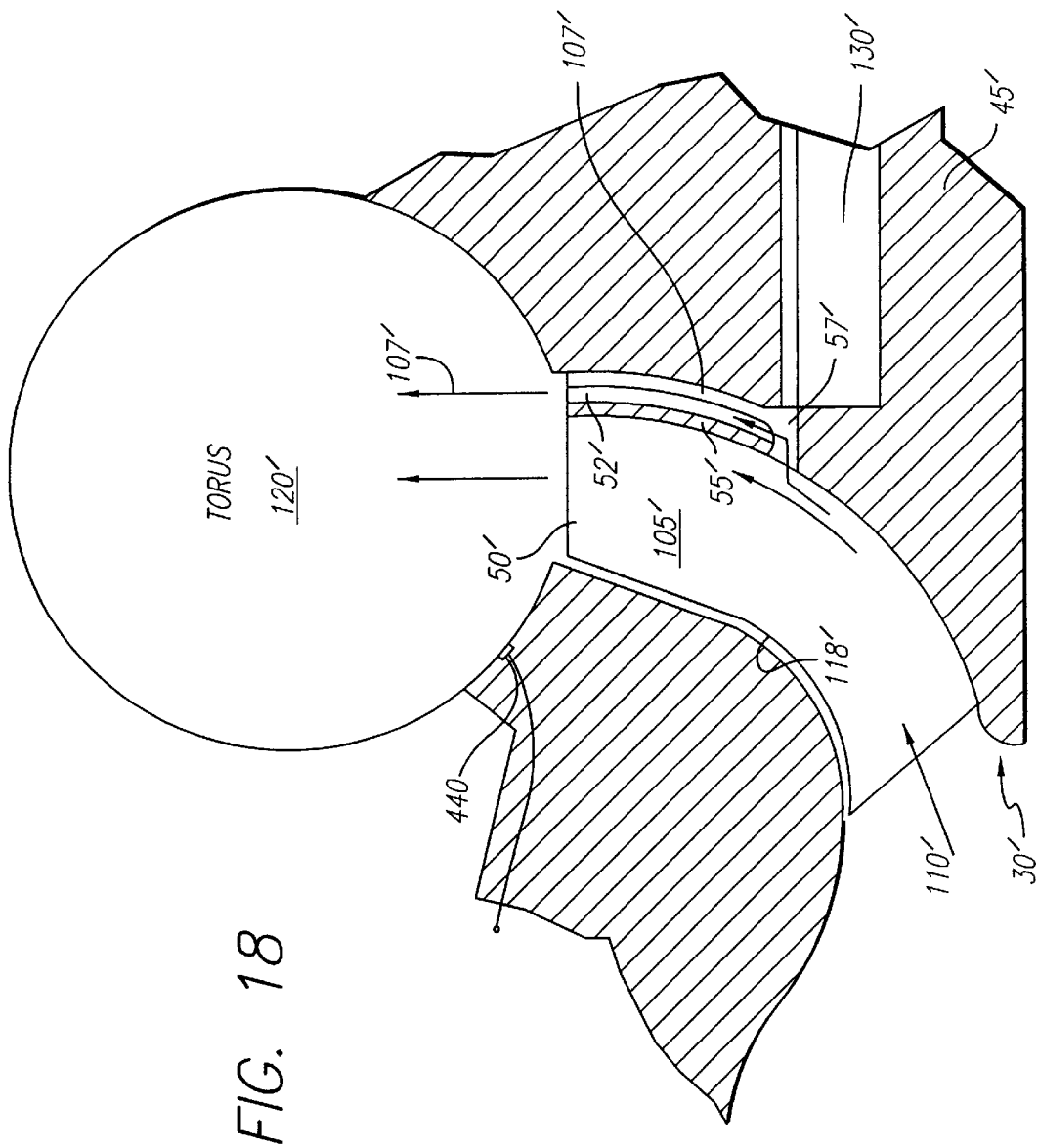
FIG. 18 is a schematic diagram of a second embodiment of a centrifugal blood pump according to the principles of the invention.

The second embodiment of the present invention is illustrated in FIG. 18. This embodiment finds substantial correspondence in structure and function to the first embodiment as illustrated in FIGS. 10 and 11. Accordingly, the structures that correspond to the structures previously discussed in connection with the first embodiment have been designated with primed reference numerals. The second embodiment employs a different structure to eliminate stagnant flow areas behind the hub disc and near the seal in a different manner. Instead of providing for recirculating fluid flow in the secondary fluid passageway, which is shown as passageway 107 in FIG. 11, the blood flow in the secondary fluid passageway travels substantially in the same direction as the blood flow in the primary fluid passageway.

As can be seen in FIG. 18, a bypass passageway 107' is provided behind the impeller hub disc 55' to bypass the main flow of blood along the front blades 50' of the impeller 30' and along the clearance 98' beside the inside of the front blades. Furthermore, back blades 52' are provided to guide blood that flows along the bypass 107'. The back blades may be curved in the same substantially curved fashion as the front blades, so that the blood in the bypass travels in substantially the same direction as the flow of blood along the front impeller blades 50'. The opening 57' in the hub disc 55' connects the primary fluid passageway 105' with the bypass passageway 107' so that fluid in the primary passageway is forced into the bypass passageway at the base of the impeller blades and flows out to the tip of the blades, substantially in the same direction as the fluid flow in the primary passageway. This direction of fluid flow in the bypass passageway stands in contrast to the direction of recirculated fluid flow in the first embodiment, where the fluid in the secondary recirculation passageway flowed counter to the direction of the fluid flow in the primary passageway. Nevertheless the identical result of eliminating stagnant flow areas behind the disc and close to the hub is achieved by the bypass passageway of the second embodiment.

Figure 19:
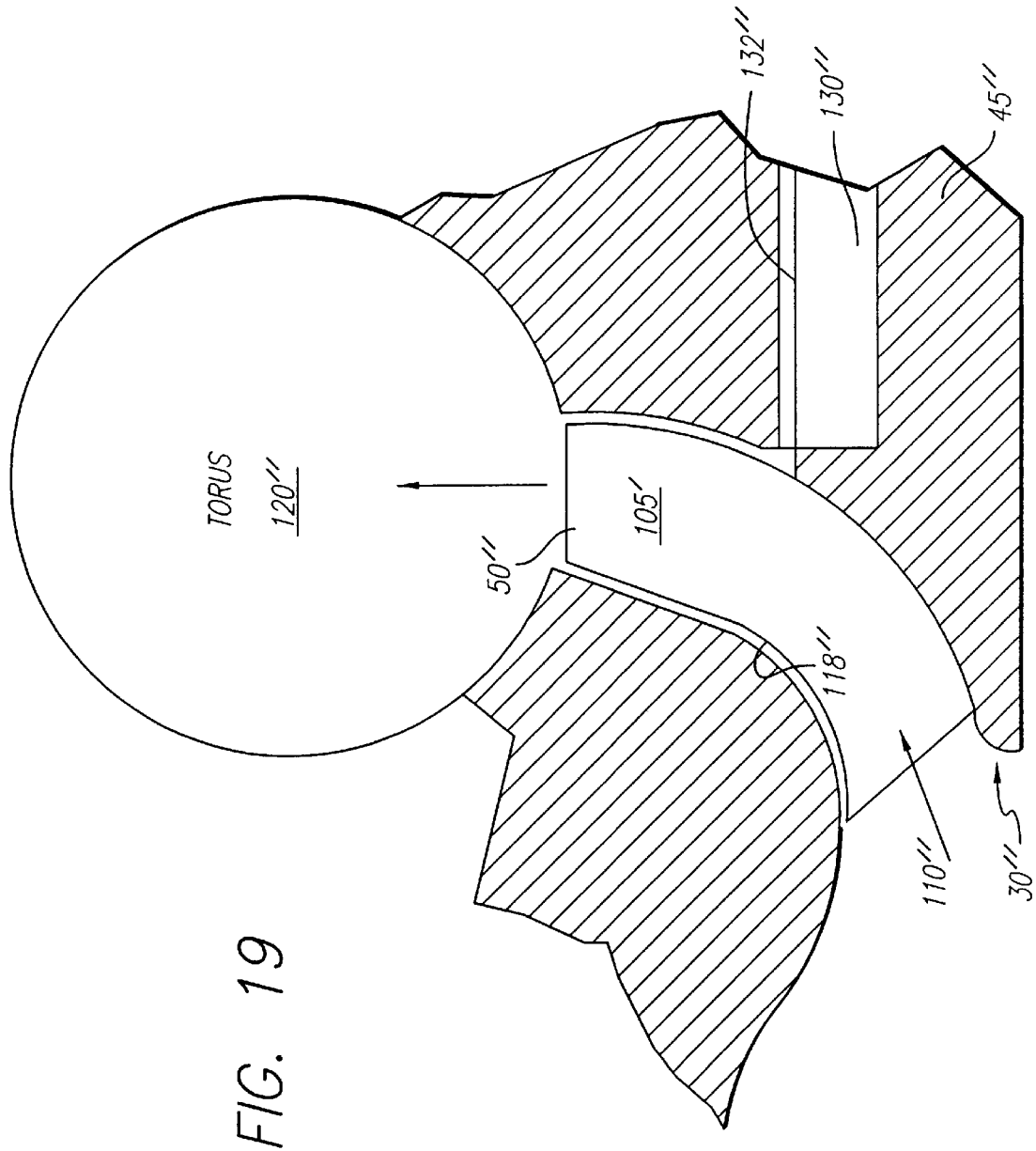
FIG. 19 is a schematic diagram of a third embodiment of a centrifugal blood pump according to the principles of the invention.

A third embodiment of the centrifugal blood pump of the present invention is illustrated in FIG. 19, with elements corresponding to those of previous embodiments identified with like reference numerals and a double prime. This third embodiment eliminates the impeller hub disc 55 of FIG. 10 and the bypass passageway 107 behind the impeller of FIG. 11 due to the fact that the impeller 30" only has blades 50" above the top diameter of the seal 130". The blades are supported by the hub 45" only extending from the inlet 110" to the top diameter 132" of the seal. Above this diameter the blades are self-supporting, designed to take the force exerted by the rotation and the fluid pressure. There is a clearance 118" between the rotating and stationary shrouds on the front side, and a clearance 119" on the back side of the blades 50" as well. These clearances should be set so that they do not cause high shear-stress level to the blood, and so that there is enough velocity provided at the hub-blade-seal interface for ventilation to the seal entrance preventing stagnation of the blood.

Figure 15:
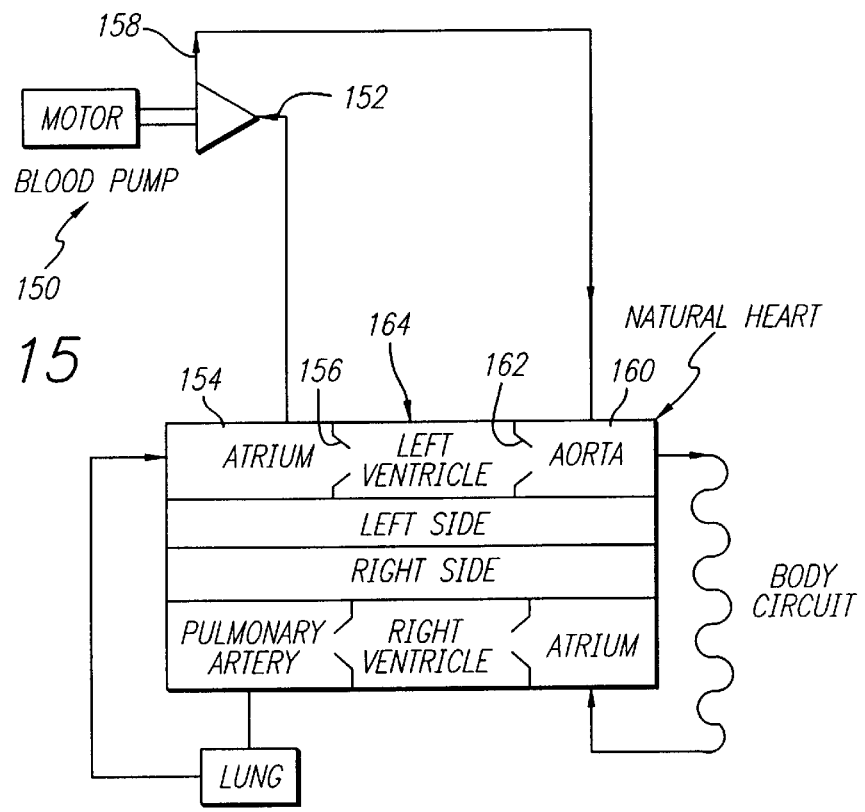
FIG. 15 is a schematic diagram of a configuration for use of the centrifugal blood pump of the invention as a single pump as a left ventricular assist device.
Figure 16:
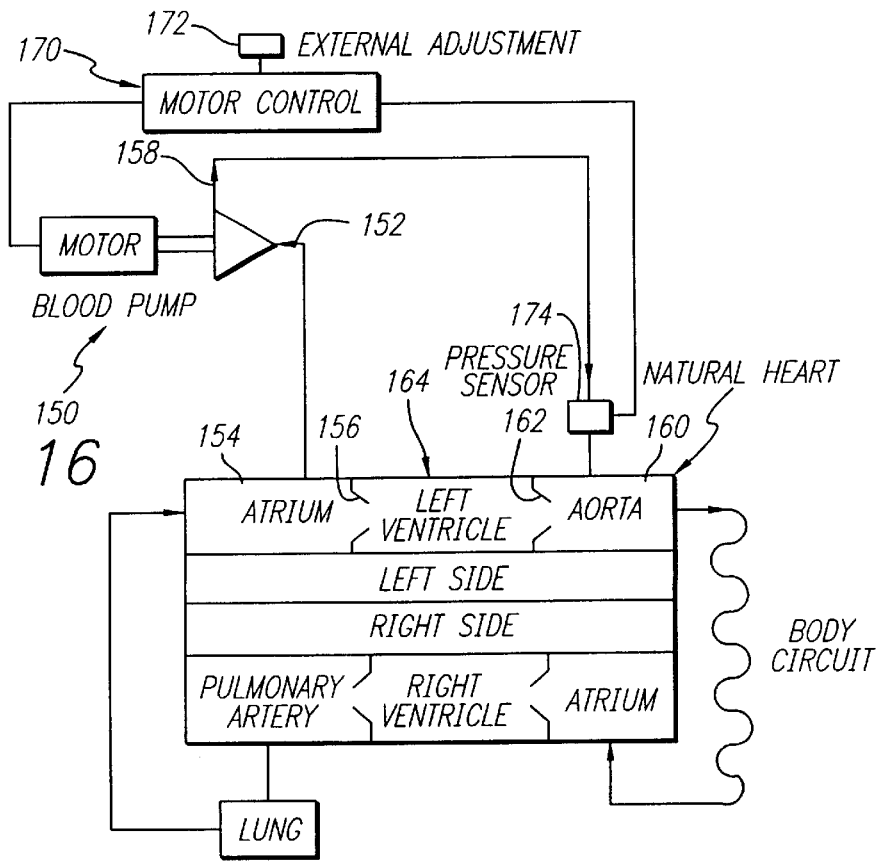
FIG. 16 is a schematic diagram of a configuration for use of the centrifugal blood pump of the invention as a left ventricular assist device with a speed control.
Figure 24:
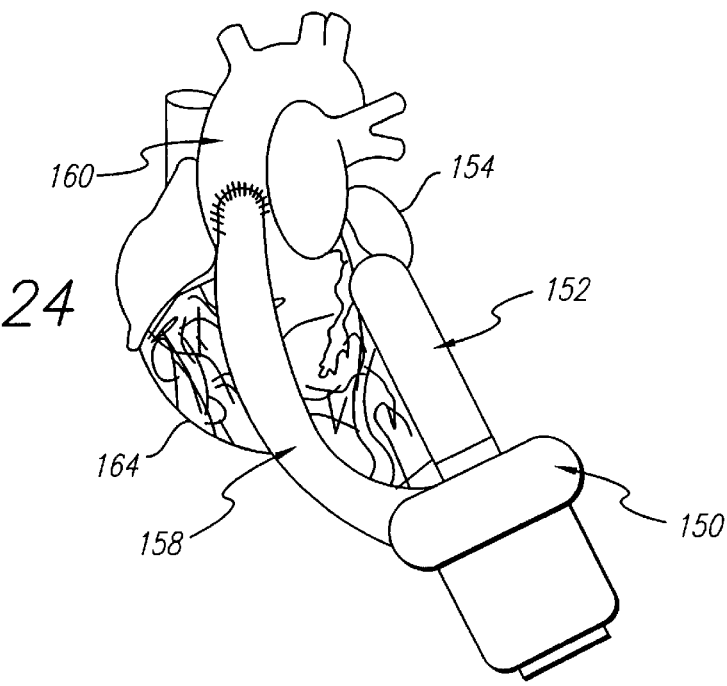
FIG. 24 shows the implantation of a Left Ventricle Assist Device (LVAD) within the human thoracic cavity in parallel with the left ventricle of the human heart.

With reference to FIGS. 15, 16 and 24, one of the first and, therefore, one of the most important applications of the centrifugal blood pump of the invention will be as a Left Ventricular Assist Device (LVAD), a temporary device to bridge the time until a final replacement heart is available. The device would not duplicate the full function of the human heart, but would only boost the left ventricular flow and pressure from the output obtained from an impaired but still functioning heart, whose reduced output by itself is insufficient. The use of a centrifugal blood pump as a LVAD is less complex than for a full service artificial heart, and hence is more reliable and less costly.

As is illustrated in FIGS. 15 and 24, when used as a LVAD, the centrifugal blood pump 150 will be used as a single pump, having inlet 152 connected to the left atrium 154 upstream of the mitral valve 156 and an outlet 158 connected to the ascending aorta 160 downstream of the aortic valve 162, thereby paralleling the function of the left ventricle 164.

If the centrifugal blood pump is used as a left ventricular assist device, no check valves or throttle type resistors in the blood stream will be required. Therefore, no additional devices are introduced that can cause blood cell damage. The simplicity of the concept of utilizing the centrifugal blood pump as a LVAD, and the attending increased reliability and reduced costs, make it attractive for cases where the atrophy of the human heart has progressed far enough to justify introduction of a bridge device, but does not yet call for the use of a total replacement with a natural or artificial heart.

A centrifugal blood pump for use as a LVAD generally also includes a motor rotational speed control 170, as is illustrated in FIG. 16. The motor speed can be selected by adjustment of a potentiometer 172, or alternatively by a digital equivalent, arranged in the electronic motor speed control circuit to be accessible for external adjustment. This external adjustment can be performed by the attending physician, or within safe limits, by the patient himself. This will allow selection of the operating speed of the centrifugal blood pump to conform to the patient activity, such as sleep, regular waking exertion, or extended exertion such as climbing stairs, and the like. As a refinement, this kind of adjustment can be automated by providing a pressure sensor 174 in the blood stream to automatically adjust the motor speed with electronic means. Adjustment within a limited range, in the sense of increasing the rotational speed, will take place if the blood pressure drops below a selected minimum value and vice versa. As an alternative to the pressure sensor, a flow sensor of the electromagnetic variety or the equivalent may be substituted. Both the pressure sensors of the flow meters can be made smooth to the blood flow to avoid fibrin build-up.

As explained above, despite the numerous advantages in size, simplicity and clean design that a centrifugal pump has over a positive displacement pump as an artificial heart, some form of programmed speed control is required to maintain the volume-flow rate in the presence of varying inlet and outlet pressures. To remedy this, a plurality of speed control concepts have been developed.

FIG. 4 shows a dual centrifugal pump apparatus without any form of speed control. Such a configuration is undesirable, since it can not or only very narrowly satisfy the needs of the human body. The need for speed control is further illustrated in FIGS. 5, 6, 22 and 23, as is further discussed below. It is, nevertheless, instructive to study this configuration in order to appreciate the need for feedback regarding speed control for the two pumps, as is illustrated in FIG. 5. Pump A drives the fluid circuit that carries oxygen-depleted blood from the body to the lungs, while pump B carries oxygen-rich blood from the lungs to the rest of the body. If the resistance in the body circuit increases, the pressure difference P4–P1 increases.

The blood flow rate and blood pressure is demanded by the human body in response to different physical activities such as rest, normal activity, moderate exercise and strenuous exertion. The values differ from one individual to the next. Typical values for healthy individuals are listed in Table 1 and are plotted in FIGS. 22 and 23.

TABLE 1

| Activity | Flow Rate 1/min | Aortic Blood Pressure mm Hg g | Pulmonary Blood Pressure mm Hg g |
| --- | --- | --- | --- |
| Rest | 6 | 110 | 10 |
| Normally active | 10 | 130 | 20 |
| Moderate exercise | 12.5 | 145 | 24 |
| Strenuous exercise | 15* | 145 | 24 |

*Maximum observed on athletes during peak performance.

Figure 13:
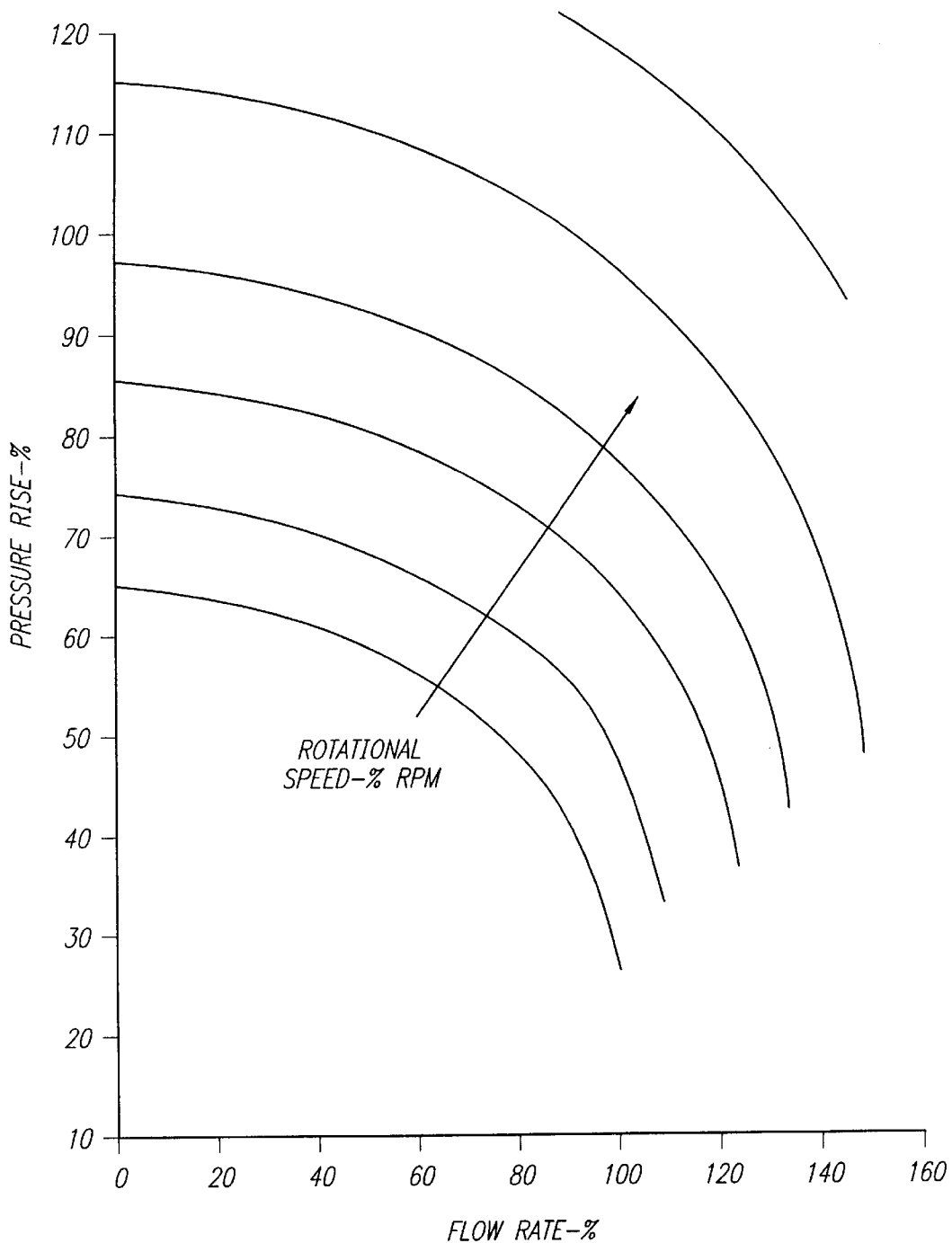
FIG. 13 is a graph of the pressure head versus volume flow rate generated at different centrifugal pump speeds plotted in percent relative to the design point.
Figure 14:
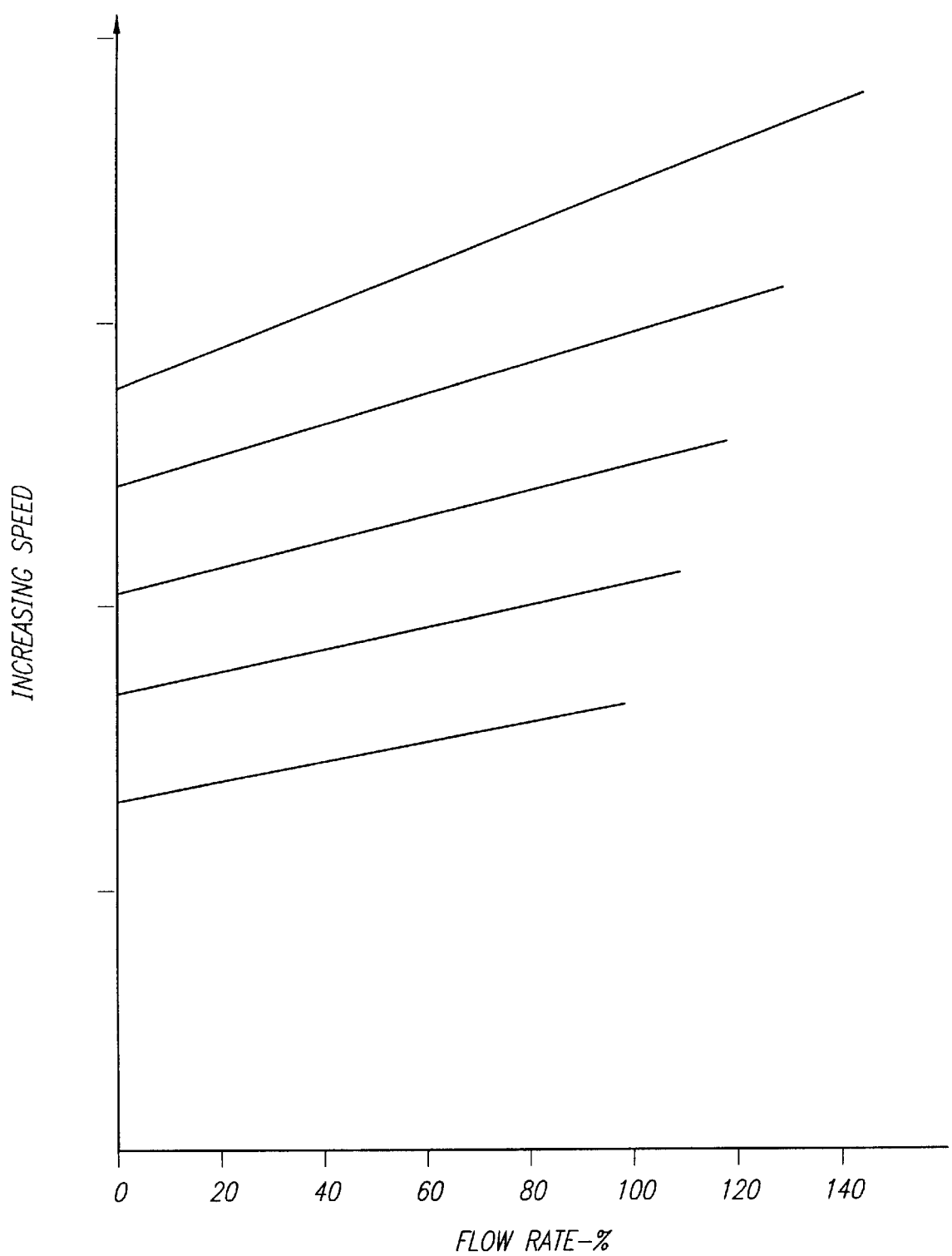
FIG. 14 is a graph of the power required at different volume flow rates and pump speeds.

While operating at constant rotational speed the characteristic of centrifugal pumps results in a drop in flow rate as the outlet pressure is increased. This characteristic, shown in FIGS. 5, 6 and 13 can be compensated for, as part of the present invention, by increasing the rotational speed of the pumps with a speed control circuit shown in FIG. 17.

Figure 12:
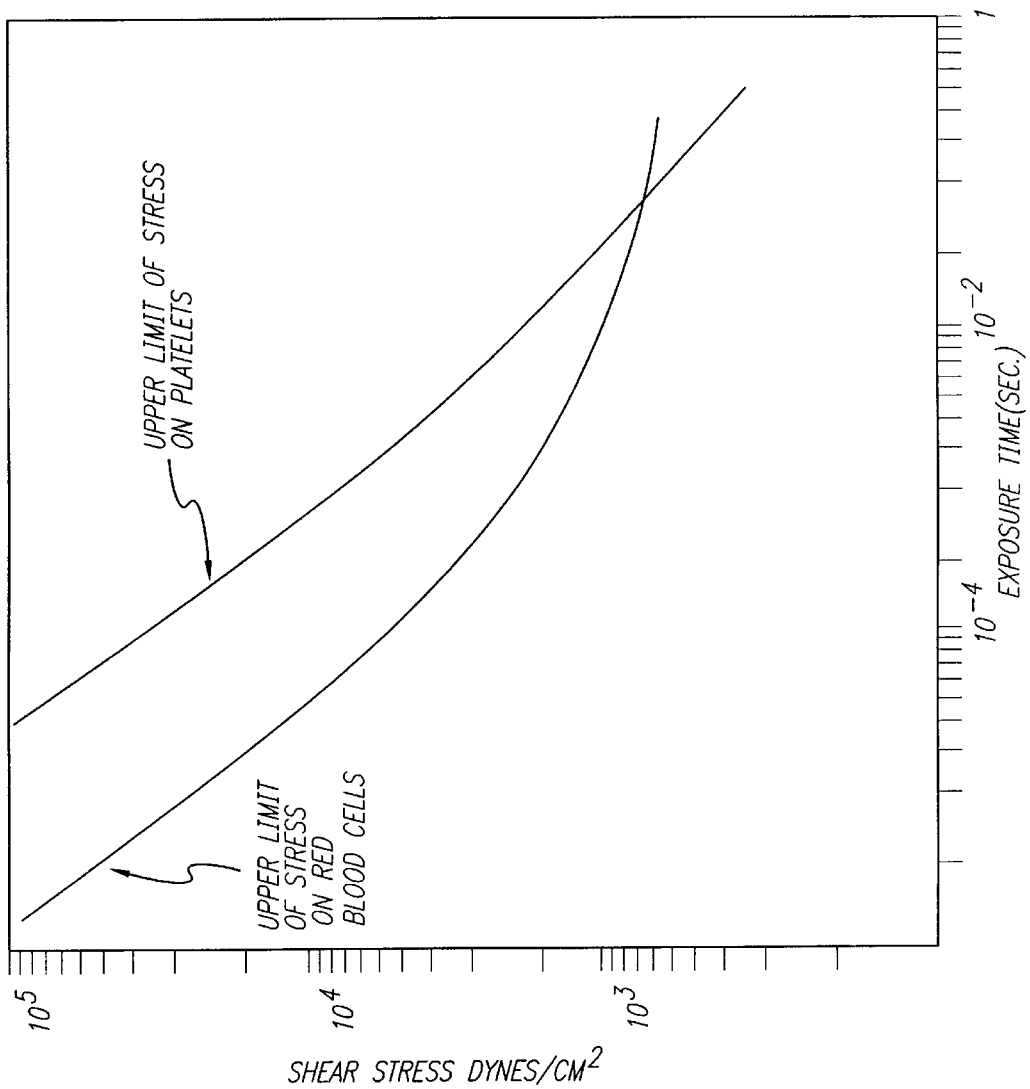
FIG. 12 is a graph of the sheer stress generated on fluid passing through the pump versus the exposure time on the fluid, from which the stress-time product is calculated.

For a given pressure rise, the pump speed must be increased as the diameter is reduced. A reduced diameter can result in increased shear stress on the blood. The general criteria that concern such stress on the blood are the blood damage limits shown in FIG. 12, illustrating the fluid stress induced lysis on red blood cells and platelets. Below the line shown for red blood cells, there will be little or no lysis of the red blood cells; and below the line for platelets, there will be little or no damage to the platelets, and thus little chance for fibrin formation. However, above those lines, damage can be expected.

One size pumping element can not satisfy the required flow rate range from a small person to a large athletic male. It is therefore desirable to cover this range with more than one pump size. For example, one size may be selected for small bodied persons, another for persons with average body weight, and a third size may cover the upper weight range. A similar constraint on size is the installation envelope (or frame size) of the heart pump dictated by the available chest cavity dimension of a particular patient. To offer the heart surgeon an adequate selection of heart pump performance and heart pump installation envelope, a plurality of scaled pumps, such as three sizes, for example, all geometrically similar in structure, can be derived by scaling from the developed prototype by a pump design specialist well versed in the art of heart pump design. Further variations reflect the general health and physical condition of the individual person and the desired or allowable level of activity. These considerations are reflected in the modular design of the heart pump which allows to cover the full range of flow required for a very light person to the upper end of the spectrum represented by large frame and heavy body weight patients. This range can be covered by a maximum of three frame sizes. The modular design will allow the cognizant cardiologist to select the heart pump's design flow rate, hence the pump geometry from a limited, preselected group of parts or preassembled centrifugal heart pumps. Additional refinements include adjustment of the flow rate, and hence, selection of the pump's geometry, considering the individual's allowable level of activity. The design of the control system also allows the cardiologist to evaluate and select the control input parameters to restrict or extend the pump's output.

Although the absolute blood flow rate varies with activity, the flow rate of both pumping elements, the left ventricle (high pressure) pump element and the right ventricle (pulmonary, low pressure) pump element must be equal during any of the individual's activities. This equality of flow must be maintained throughout the range of operation and is an important consideration for the design of the control system for this artificial heart pump, and forms an important consideration of this invention.

Figure 17:
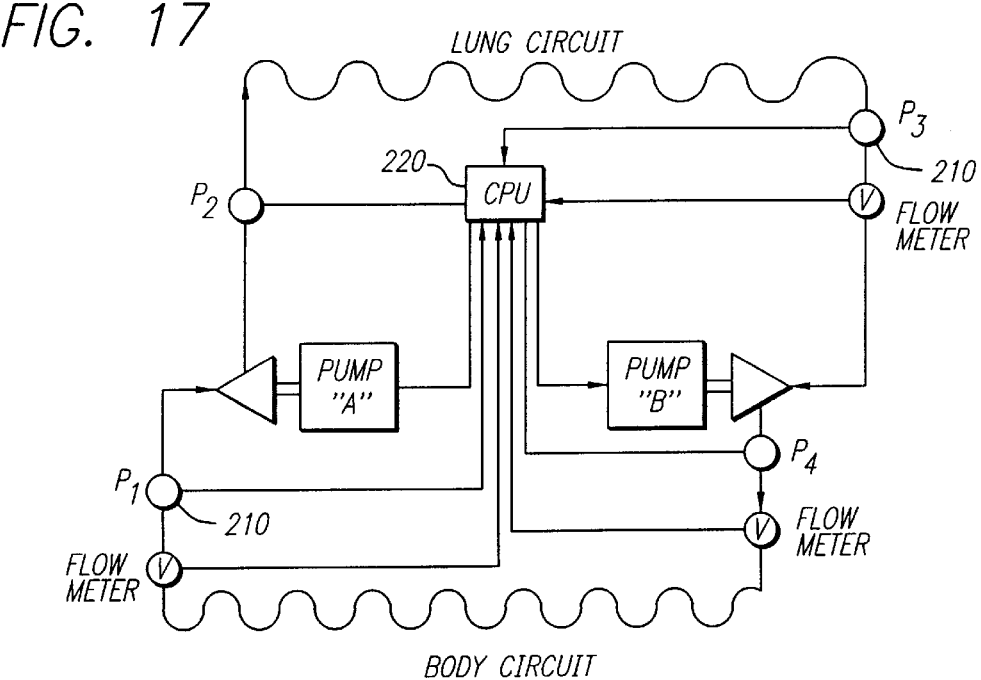
FIG. 17 shows a dual centrifugal heart pump system according to the principles of the invention with speed control.

Variation of the blood pressure and blood flow rate results from dilation or contraction of the blood vessels in response to a particular activity such as rest or strenuous exercise. From FIGS. 5, 6 and 23, it is evident that variation of the pump rotational speed is needed to satisfy the blood pressure, and hence, the blood flow demand for a given activity. Such a rotational speed control system can take many forms, as it can be realized by experts in the art of fluid control system designs. Such speed control systems may be based on electronic analog or all digital speed controls interfacing with the motor's electronic commutation circuit with control inputs provided by electronic pressure, temperature, flow and rotational speed sensors. Referring to FIG. 17, in one presently preferred embodiment of such an exemplary speed control system, two pressure sensors 210 can be employed to measure the pressure and volume flow rates at point P1, the inlet of pump A, and point P3, the inlet of pump B. Alternatively, a differential pressure sensor 211 with one pressure sensor and one flow rate sensor or flow meter 215 for each pump may be used. The pressure sensors are typically pressure transducers, and the flow meters can be magnetic flow meters that do not obstruct the flow, as known in the art of fluid dynamics for medical applications. A controller 220, such as a microprocessor, samples data sensed by the flowmeters and/or pressure transducers to control the pumps.

The flow rate, which results from the given activity level as a function of the dilation or contraction of the blood vessels, is preferably measured at the inlet of the left ventricle heart pump, pump B, but may also be measured at the outlet. This pump is the primary pump. If the output differential pressure does not agree with the desired pressure that corresponds to the particular flow rate (as illustrated in Table 1 and FIG. 22), the rotational speed of pump B is adjusted by the control system without conscious human intervention. Conversely, with different degrees of sophistication, the control system may be configured to allow a limited override by the cognizant physician, or by the patient.

The flow rate of pump element A, the pulmonary pump, the slave pump, is controlled by the control system to match that of the primary pump, pump B, the left ventricular pump. The output pressure or differential pressure of the slave or pulmonary pump may not be controlled, but results from the resistance of the lung circuit. The programming may be done by people conversed in the art of control system designs for medical purposes with software or firmware (permanently programmed computer chips) on which the blood differential pressure for the corresponding different flow rates is stored in a look-up table, or the equivalent. The maximum rotational speed may be limited by the control software to maintain safe and efficient operation without excessive power consumption and heating. Additional parameters may be introduced for control and safety purposes such as limiting the maximum flow rate, or limiting the maximum output pressure or differential pressure which would override the programmed output differential pressure. Other restrictions are operating temperature, and run time in the higher power regime. A further constraint imposed on the control system may be a restricted operating envelope (pressure and flow rate), selectable as external input to the control system by the cognizant physician in consideration of the individual patient's general and specific health.

Figure 22:
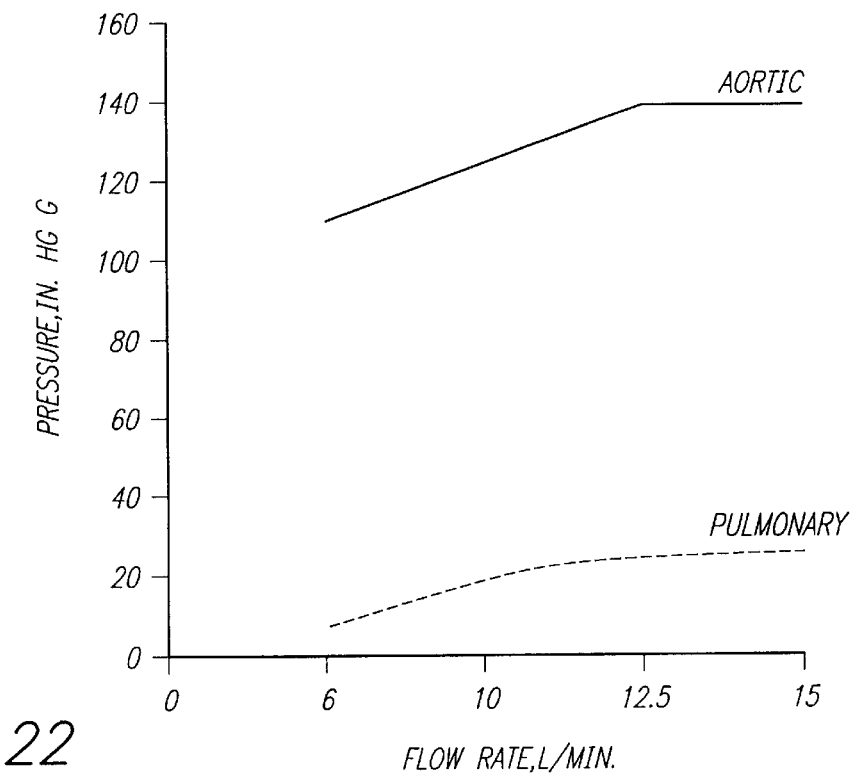
FIG. 22 is a graph showing the typical blood flow rate of healthy human males from rest to strenuous exercise as tabulated in Table 1.
Figure 23:
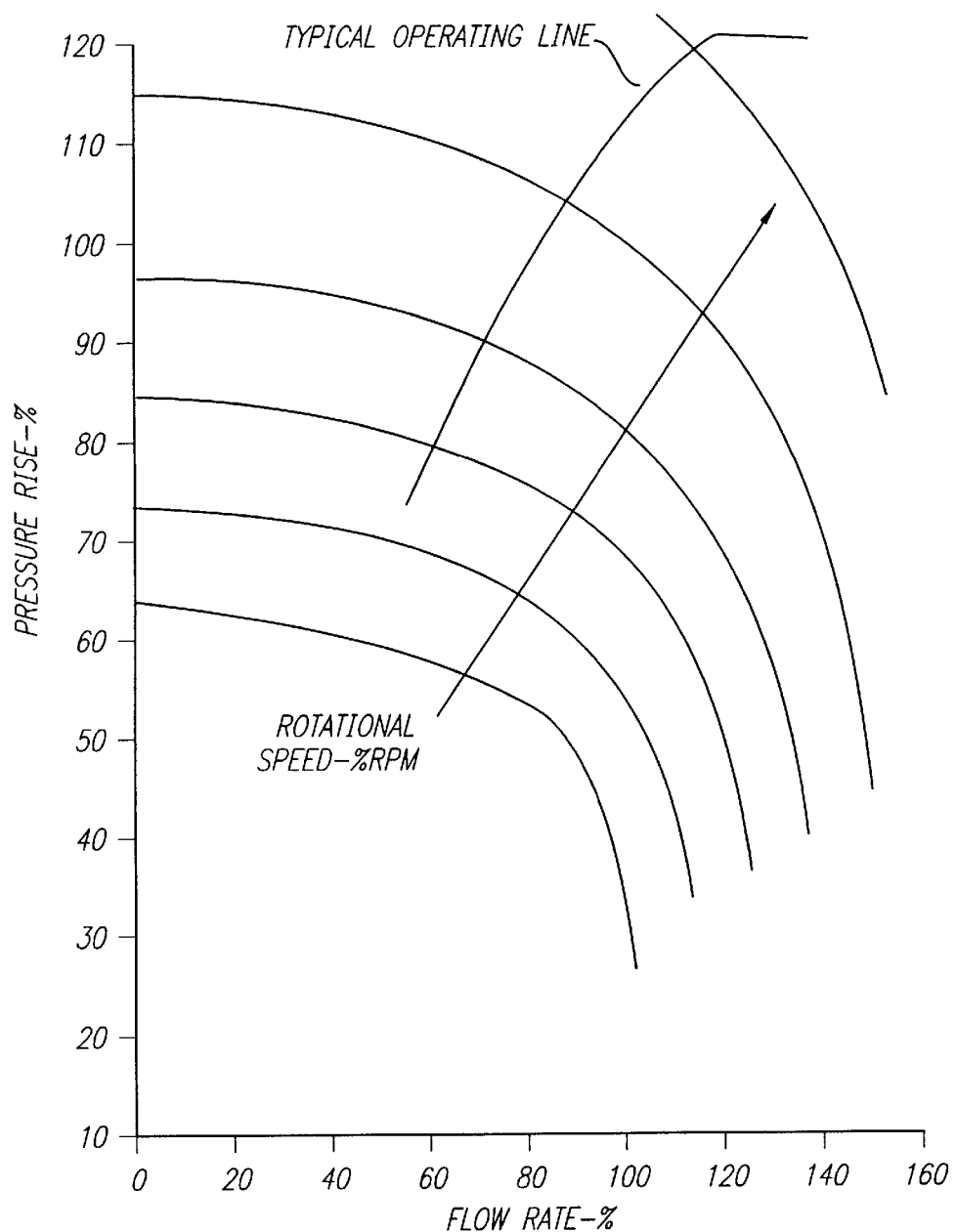
FIG. 23 shows a performance map of a centrifugal blood pump element with superposed blood flow rates and pressure rise of FIG. 22, plotted in per cent of the design point values.

If, from a steady state operating point, the blood pressure increases or decreases as a result of the human body's adjustment of the dilation or contraction of the blood vessels resulting from a change in exertion, the rotational speed of the heart pump B in the body circuit is increased as required by the pressure versus flow rate characteristic programmed in the microprocessor (as illustrated in Table 1, and FIGS. 22 and 23). This will correspondingly increase or decrease the flow rate until the controller achieves a new equilibrium.

The flow rate in the lung circuit must be made the same as the flow rate in the body circuit, as explained above. The control system thus will adjust the rotational speed of heart pump A either lower or higher until the flow rate in the lung circuit is the same as in the body circuit. The output pressure of pump A will not be controlled by the control system, but will be the natural pressure resulting from the dilation or contraction of the blood vessels in the lung circuit. A maximum pressure limiter and/or warning device may be included to warn the patient and/or the cognizant physician.

The overall operation of the sampling of data and control of the pumps can be coordinated by any suitable processor, as is well known per se to those skilled in the art of control theory in fluid circuits.

The motor is tightly integrated into the overall pump design and mechanically and electrically optimized for this special application. All the waste heat produced by the blood pump is rejected within the body to avoid extra-corporeal cooling conduits. The primary sources of waste heat are the motor, bearings and shaft seal. Hot spots must be avoided. Blood must be kept away from the motor cavity because of the potential for fibrin formation in the motor cavity and to avoid excessive friction losses. The solution to these problems is a fundamental aspect of the design of the centrifugal blood pump and has a major effect on the function and ultimate success of the device.

A heat transport fluid, either gaseous or liquid, is circulated within the motor and bearing chamber to collect the waste heat composed of a) the motor electrical, mechanical and windage losses, b) the bearing losses, and c) indirectly, the friction losses of the shaft seal. The waste heat is transported to the pump surfaces that contact the blood and to the exterior surfaces of the pump covered by tissue. The pump and motor assembly are currently preferably internally liquid cooled, preferably with aqueous saline solution, and waste heat conducted by the internal heat transport fluid to the pump surfaces is transferred to the blood flowing within the pump and the tissues covering the pump.

Figure 21:
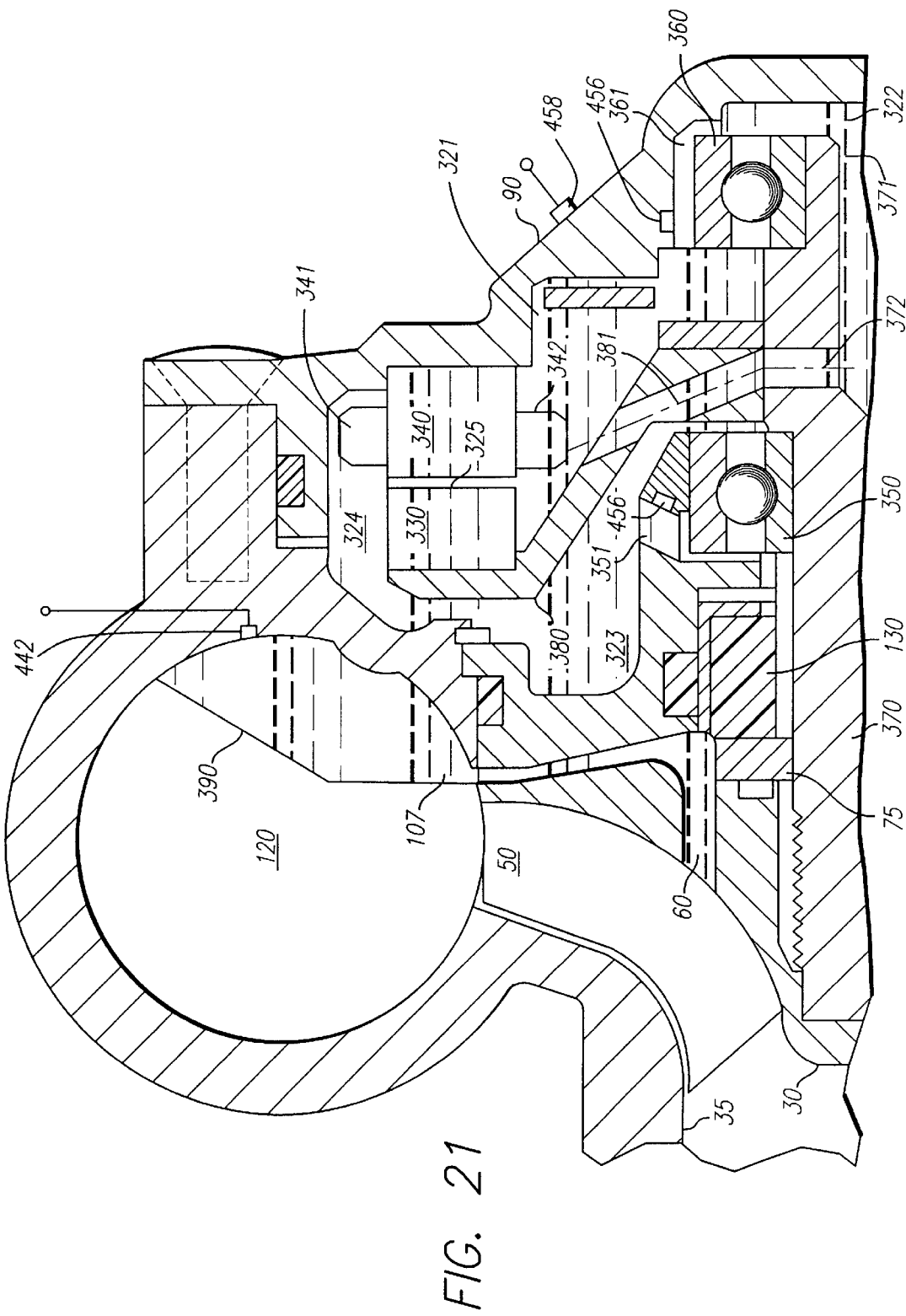
FIG. 21 is a schematic diagram of this cooling loop and heat transfer regions from the motor of the centrifugal blood pump of the invention.

An exemplary cooling loop for the motor of the centrifugal blood pump is illustrated in FIG. 21. The shaded area 321 shows the cooling loop for the flow of the internal heat transport fluid, and the shaded area 390 shows the surface area where most of the heat is rejected from the pump surfaces to the blood stream.

Cooling of the motor rotor and stator is necessary. For this purpose the motor cavity may be filled with a liquid, such as aqueous saline solution, which is currently preferred, or alternatively an inert gas (e.g., helium) or another gas compatible with the human body, e.g., $CO_2$ or $NO_2$. One disadvantage of filling the motor cavity with a gas at atmospheric pressure is the limited heat transfer rate available to transport the waste heat from the motor to the surfaces of the heart pump that are contacted a) by blood and b) by tissue which act as heat sinks.

For a typical application as a bridge device, gas cooling of the motor is adequate. Advanced applications that would give the recipient of the heart pump more liberties of motion—e.g., airplane flight or mountain ascent—may require a more refined cooling concept. This is primarily because of a potential difference in pressure at high altitudes between the blood circuit and the motor cavity that was charged a lower altitude, which can cause the motor cavity to be at higher pressure than the diastolic pressure in the blood circuit at a higher altitude. If the shaft seal should be in an incipient failure mode, that is allowing gas to leak out of the motor cavity into the blood stream, the motor cavity pressure would be reduced, potentially reducing heat transfer from the motor and overheating the motor. Additionally, depending on the selected gas, entry of gas into the blood stream in case of a seal failure could cause further complications.

Therefore, the heat transfer from the motor may be improved by filling the motor cavity with an aqueous saline solution that is not subject to expansion and compression at altitude and thus tends not to escape through the shaft seal interface. Improved heat transfer during all operational phases results from the use of the liquid saline solution as compared to a gaseous heat transport fluid. An additional benefit from the use of saline solution as a heat transport fluid is that if the seal should leak and allow the cooling fluid to enter the blood stream the cooling fluid is biocompatible. To prevent electrical short circuits, the electrical and electronic components arranged within the motor cavity are typically embedded in an insulation potting compound that provides electrical isolation without unduly restricting the heat transfer. Additionally, the motor voltage is low enough to avoid an electric shock if the insulation should break down.

Figure 20:
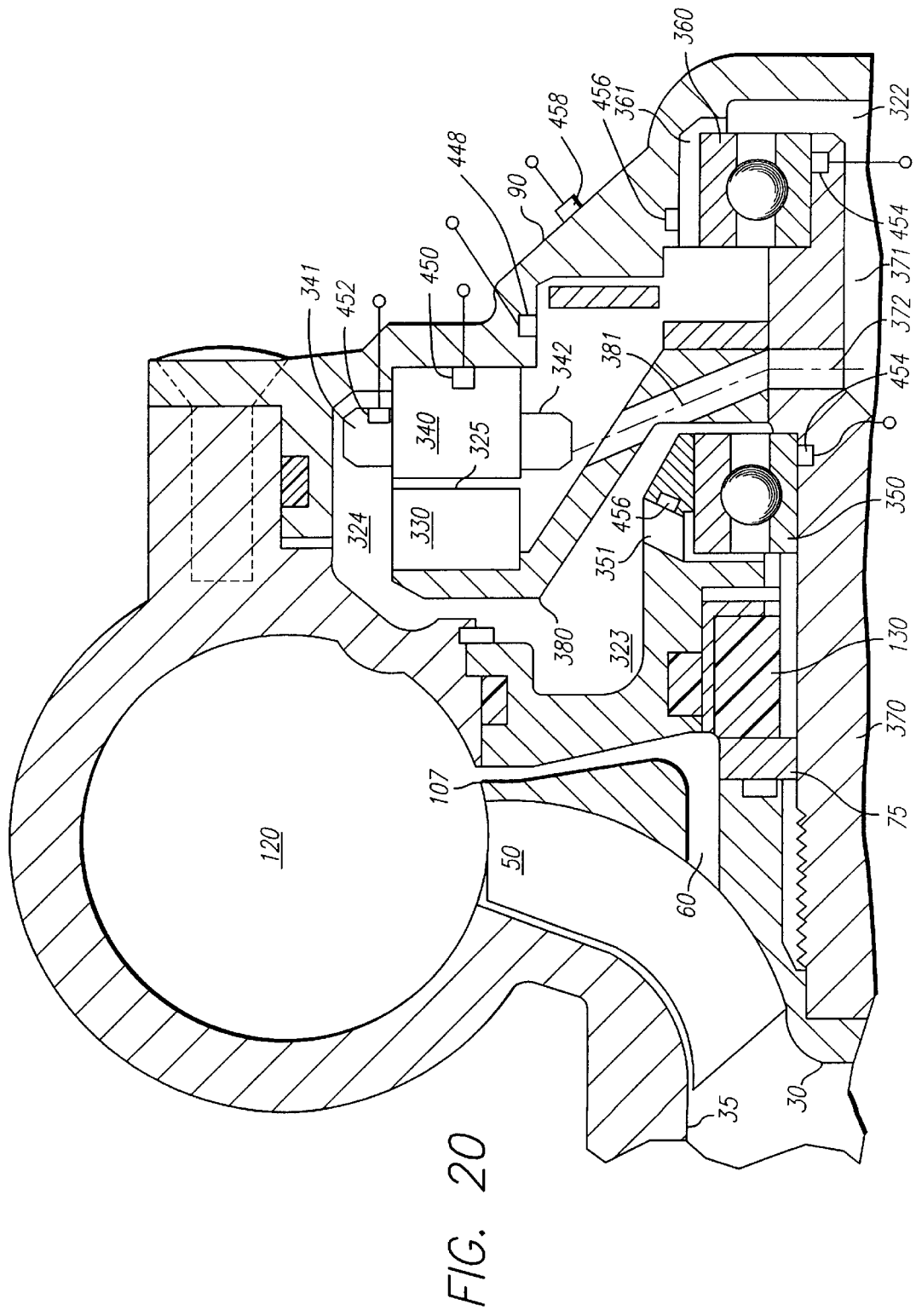
FIG. 20 is a schematic diagram of an alternate motor arrangement suitable to fit the space availabe in the human body, showing the cooling fluid flow path of the motor of the centrifugal blood pump of the invention.

With reference to FIGS. 20 and 21, the heat transport and cooling fluid, either gaseous or liquid, typically fills the motor cavity in the motor housing 90, illustrated by the shaded area 321. Referring to FIG. 20, the producers of waste heat are typically the motor rotor 330, the motor stator 340 and the bearings 350 and 360. The shaft 370 (or 63 of FIG. 10) is equipped with a central bore 371 and one or more radial bores 372. Similar radial bores 381 are included in the motor disk 380. The bores 372 and 381 rotate while the motor is turning, producing a differential pressure in the cooling fluid due to the centrifugal force imparted on the cooling fluid during rotation. This differential pressure propels the cooling fluid through the bores 372 and 381, and hence, throughout the cooling circuit illustrated by the shaded area 321 of FIG. 21. Bores 371, 372 and 381 therefore comprise a cooling pump. A similar effect can be obtained by substituting blades for the bores 382.

The bearings 350 and 360 are also cooled by branches of the cooling circuit. Rotation of the bearings assist the flow through the bearings. Bores 351 and slots 361 are provided to effect an efficient flow through and around the bearings.

Specifically, because of this centrifugal force induced differential pressure, the cooling fluid enters the bore 371 from the cavity 322 and is discharged from the bore 381 of the cooling pump. At this point the cooling stream discharged from the bearing 350 at bore 351 is picked up. Rotation of the rotor disk 380 further propels the cooling flow through cavity 323 into cavity 324 at the outer diameter of the motor, where the outboard motor end coils 341 are cooled. From there the flow progresses inward along the motor stator into the clearance space 325 from where heat from the motor rotor 330, the motor stator 340 and the inboard stator end coils 342 is absorbed.

Progressing inward toward the bearing 360 the flow of the transport fluid splits; one branch cooling the outer race of the bearing through slot 361 and the outer branch traversing the bearing 360. If a shielded bearing is used, e.g., if the transport fluid is gaseous, the flow branch through the bearing is small and most of the heat from the bearing is removed from the outer race at slots 351 and 361. A wave spring bushing or similar spring sleeve or bushing may be substituted for the slot 361. If such a spring sleeve is used it will have the dual function of providing a flow path for the cooling fluid as well as being a flexible bearing mount, helpful to reduce vibrations induced by the motor rotation. After passing the bearing 360 the cooling flow enters the cavity 322 from where the cooling cycle starts anew.

Referring to FIGS. 10, 20 and 21, the heat collected by the cooling stream is discharged along the area 390 torus 120 serving as a heat collector, and also along the recirculation slot 107 and 60. Further heat transfer to the body takes place along the outer surfaces of the motor housing 90 and 120. The heat flux through the housing wall to surrounding tissue can be controlled by thermal barrier coatings. An additional portion of the rotor heat, bearing and seal heat rejection is conducted along the shaft 370 and recirculation slot 107 into the blood stream passing along surfaces of hub 45 and 30.

Coatings may be applied to certain surfaces of the pump and motor housings. The purpose of such coatings can be to modify the surfaces of parts to enhance biocompatibility, achieve bioactive surfaces (e.g., antithrombogenic coatings), permit diffusion of adjacent tissue into the exterior surfaces of the blood pump, or reduce heat transfer locally with thermal insulation coatings.

Such coatings typically can be applied to parts of the pump and motor housings by plasma spraying of specially selected powders, vapor deposition, or the equivalent. The desired material is heated in a high temperature gas plasma jet and propelled by the plasma onto the surface to be treated. Due to the temperature of the gas the sprayed material is in a plastic state and adheres and binds to the target surface by impact without subjecting the target part to any appreciable heat buildup during the coating application. To achieve the desired effect, different materials in powder form can be plasma sprayed concurrently by applying a powder mix or may be applied progressively, with the most desirable material at the blood interface. For example, a composite surface build-up can consist of zirconia or modified zirconia used for thermal insulation, followed by a sealing coating and an antithrombogenic coating. Therefore, by judicious selection of the coating powders this process is ideally suited for modifying certain geometric surfaces of the blood pump.

To limit the temperature of outside surfaces of the pump housing in the vicinity of the heat source (motor stator), strategically located surfaces may be covered by a thermal insulation coating. The heat flux through the housing walls to the surrounding tissue can be controlled by application of biologically compatible coatings with an effect on heat transfer similar to the effect of zirconia. Such coatings can be tailor made to enhance the biological diffusion of tissue.

One example of such a coating is the hydroxylapatite coating applied by Sulzer Plasma Technique, Inc. onto surgical implant surfaces. Another example is the application of specially engineered antithrombins by Metro—Line—Industries, Inc.

The application of the desired coatings is not limited to plasma spray, and other coating application processes may be used, such as the Fast Atom Beam process by Ion Tech Limited, or vapor deposition done in a vacuum.

With the centrifugal blood pump of the invention, it also is possible to provide for a pulsating blood flow. The need for pulsating flow has been assessed differently by different researchers. While some authorities feel that pulsing is not needed, at least in the short run, other authorities in the field assert that the lack of pulsing can detrimentally affect other organs such as the kidneys.

To provide for cases where pulsing is desired, the control system can be equipped with a control of the rotational speed that provides for a periodic variation of the rotational speed of the pump. It is recognized that if pulsing of the blood flow is thought to be needed for the well-being of other organs, such pulsing would not have to simulate exactly the function of the human heart. The pulse frequency may be lower and the pulse wave shape may be different from those of a normal heart function, with the main emphasis being the periodic, limited change in pressure. Such a periodic change may be accomplished by superposition of a square wave (on-off bias signal) to the motor input current and/or voltage. The inertia of the motor and pump rotor will smooth out the resulting step transient and limit cycle. The rotational speed of the pump could also be changed by superposition of a low frequency sinusoidal wave to the motor input current and/or voltage.

It should be recognized that the axial length of the blood pump is also extremely important for the ease of insertion into the patient and for the well-being of the patient. Therefore, to achieve a shorter motor length and, hence, a shorter overall length of the pump assembly, the motor rotor is preferably configured as a bell shaped rotor disk 380. This allows part of the seal, bearing housing and the inboard bearing to be tucked inside of the bell shaped rotor disk 380, thereby reducing the axial length of the assembly. With reference to FIGS. 20 and 21, this rotor shape is defined as containing a) a bell shaped portion of the rotor disk 380; b) a rim at the outside portion of the bell shaped disk that is configured to accept the electromagnetic or magnetic portion of the motor rotor; and c) a hub 382 in the center of the bell shaped motor rotor 380. Shown in FIG. 20 is a configuration designed to accept flat permanent magnets. The configuration is not limited to flat magnets, e.g., cylindrical magnets inserted through bores in the rim may be used or otherwise suitably attached to the rim. Alternatively other magnet geometries may be used or the rim may be configured for conventional electromagnetic motor elements. The hub in the center of the bell shaped motor rotor may contain means for transferring the motor torque to a shaft or to any means connecting the pump rotor to the motor rotor. The hub can be equipped with splines connected to a shaft that is similarly equipped. Alternatively, any applicable traditional means of connecting a rotor to a shaft or to another rotor may be employed. Such other means are keys, pins, torque rings and other means conventionally used to transmit torque.

The frequency of the alternating current (which may be converted DC current as used typically in brushless DC motors) can be selected to be compatible with the desired rotational speed and the selected number and configuration of the magnets as conventionally done by persons skilled in the art of electric motor design and electronic control circuits. The selected frequency and magnet configuration can be optimized to satisfy the hydrodynamic performance requirement and to result in the most desirable overall package dimension for easy accommodation of the heart pump within or in the immediate vicinity of the human body.

One application of the centrifugal heart blood pump configured according to the embodiment of the invention can be applied as a Left Ventricle Assist Device (LVAD), as illustrated in FIGS. 15 and 24. It would be implanted within the thoracic cavity, somewhat posterior to the left apex of the heart. Inlet blood would be drawn into the suction side of the pump from the left ventricle/left atrium. The discharge side of the pump would provide supplemental and supportive perfusion to the ascending aorta above the aortic cusps. The pressure and flow would be selected to assist the normal myocardial tissue in supplying blood flow to the cardiovascular system.

This implementation of the LVAD would be best employed as a bridge device to support those patients exhibiting life threatening cardiac insufficiencies. This physiological condition exists when the heart fails to supply adequate systemic perfusion. This technique would allow the patient to regain cardiac health while awaiting a donor's heart. It is speculative that this could be a protracted method of cardiac support. With the inadequate supply of donor hearts, it has become evident that such a surgical technique could not only provide cardiac rejuvenation, but may be an acceptable method of allowing the patient to assume a reasonable quality of life.

Figure 26:
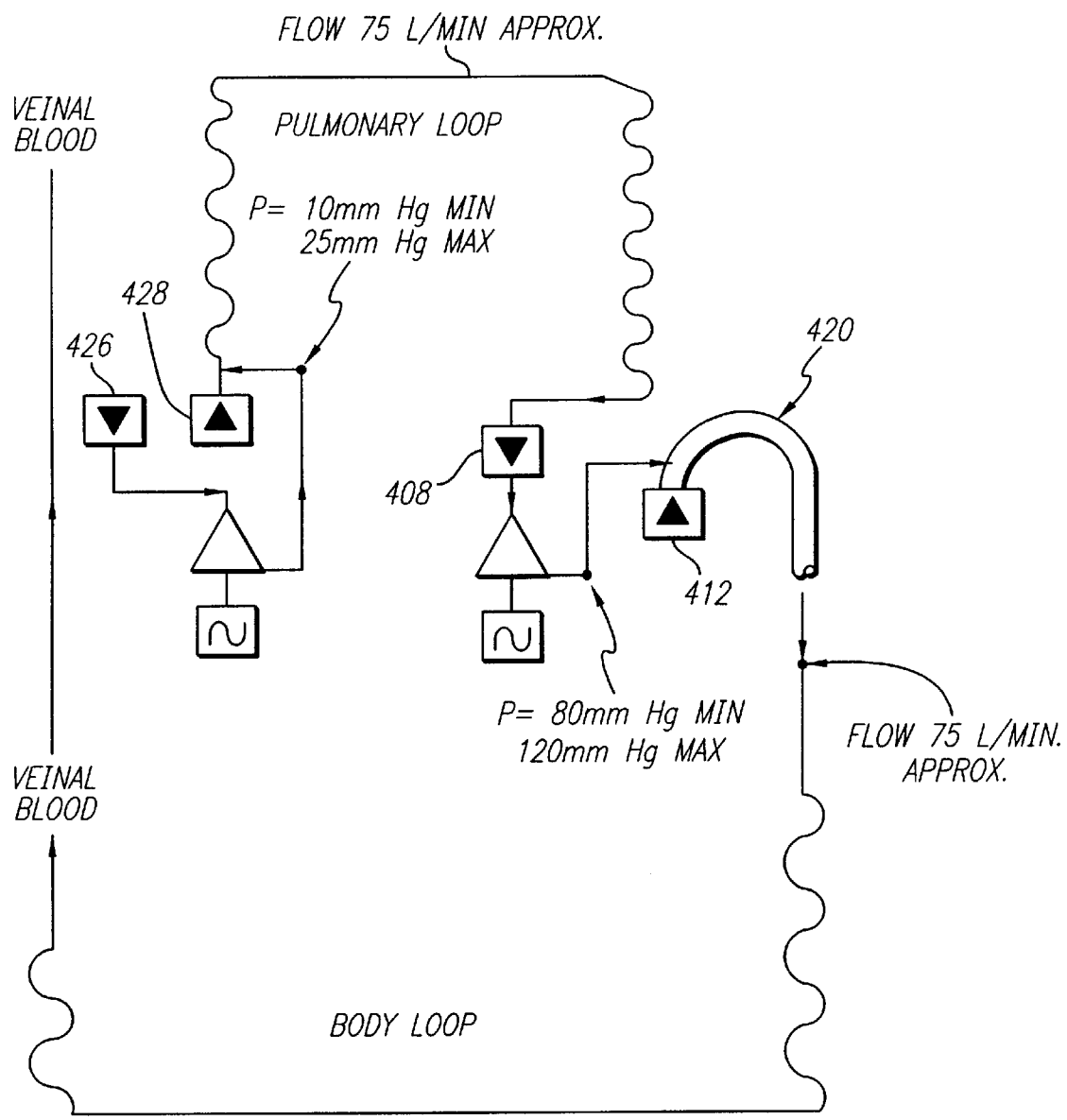
FIG. 26 is a schematic diagram of the Total Artificial Heart shown in FIG. 25.

Application of the centrifugal blood pump configured according to this invention can be employed as a Total Artificial Heart (TAH) 400. With reference to FIGS. 25 and 26, two centrifugal blood pumps will be used, one 402 configured to supply the left ventricular flow, and the other 404 to supply the pulmonary flow. The anastomosis would utilize the patient's own atrial chambers. The inlet 406 to the left ventricular pump (high pressure pump) would be connected to the myocardial tissue 408 at the apex of the left ventricle below the aortic (tricuspid) valve 410 and the mitral (bicuspid) valve 412 using a cuff 414 made from biocompatible plastic material, mostly woven or knitted polyester, such as that available under the trademark "DACRON" from DuPont, or similar suitable material. The material may also treated with a surface treatment to enhance bonding and anchoring to the body tissue. A blood tight connection will typically be crafted by the cardiosurgeon by suturing the cuff 414 to the tissue. The cuff may be connected to the centrifugal blood pump inlet 406 with a ring (not shown) made from shape memory alloy or similar material. Conventional methods employed by the surgical profession are also feasible for this purpose. The outlet 416 of this blood pump 402 will be connected by cardiac graft tubing 418 made from similar material sutured to the ascending aorta 420. The inlet 422 of the pulmonary pump (low pressure) 404 would similarly be sutured to the atrial tissue 424 below the atrioventricular valve (tricuspid) 426 and the pulmonary (bicuspid) valve 428. The outlet 430 of this pump would be connected to the pulmonary artery 432 using a similar technique as described above. This method utilizes the patient's own atrial chambers and drastically reduces complications by using the four existing human heart valves.

Another presently preferred embodiment of the invention provides means to detect the temperature of the blood passing through the blood pump. The temperature, as is well recognized, is of vital importance and, therefore, should be monitored to remain within safe and comfortable limits. In addition, the temperature signal may be used to override the motor control inputs to the CPU or modulate the motor speed control. This is of particular importance where the blood pump rotational speed, and hence, output pressure, is allowed to increase in response to the dilation of blood vessels resulting from increased patient activity, discussed above. This is done in accordance with instrumentation and control system techniques familiar to persons well versed in the art of instrumentation and control system design. The temperature sensors may be thermocouples or thermistors or the equivalent. These can be made very small, and may be embedded in the walls of parts of the blood pump directly exposed to the flow of blood. Being flush with the wall, the temperature sensors, therefore, do not protrude into the blood stream and do not cause any flow disturbance or turbulence that may be damaging to the blood but are completely isolated from the blood. The outer surface of the sensors and the embedding compound, is made from biologically compatible materials, e.g. medical grade polyester or polyester based potting compound. In one presently preferred embodiment, a blood temperature sensor 440 can be located on the inside of torus 120, as shown in FIG. 10, or the inside of torus 120' shown in FIG. 18. In an alternative preferred embodiment, a blood temperature sensor 442 can be located on the wall in the heat rejection area 390 shown in FIG. 21. In another alternative preferred embodiment, a blood temperature sensor 444 can be located on the inside of the outlet duct 42, as shown in FIG. 9. Alternatively, a blood temperature sensor 446 may be located on the wall of the recirculation passage 107, as is illustrated in FIG. 11.

In addition to being embedded flush in the walls of the blood flow passages, the sensors may be coated with a biocompatible and antithrombogenic coating as is described above. Temperature sensors may also be used to monitor safe operation of the motor and temperature of the cooling fluid, described above. The techniques are well understood by experts in the field of fine mechanical, hydraulic, electrical and electronic component and instrumentation design. The location of these sensors 448 is typically internal to the motor housing 90, shown in FIGS. 10 and 20.

For direct monitoring of the motor temperature, a temperature sensor 450 can be embedded in the stator 340. Alternatively, a temperature sensor 452 can be embedded in the stator windings 341, illustrated in FIG. 20. Similarly, the bearing temperature can be sensed by placing a sensor 454 adjacent to the outer race of bearing 350 and 360, shown in FIG. 20. Alternatively, a temperature sensor 456 can be placed in the cooling passage 351 or 361 illustrated in FIGS. 20 and 21. Similar to the flush mounted sensors in the blood stream described above, temperature sensors 458 may be placed on the outside of the motor housing 90, shown in FIGS. 10, 20 and 21, and can be coated with a biocompatible coating.

The CPU and all wiring from the sensors to the CPU may be internal to the blood pump apparatus, and do not directly interface or interfere with the patient in any form. Therefore, biocompatibility of the sensor wiring is not a requirement and may be subordinated to considerations of longevity and reliability.

It will be apparent from the foregoing that, while particular forms of the invention have been illustrated and described, various modifications can be made without departing from the spirit and scope of the invention. Accordingly, it is not intended that the invention be limited, except as by the appended claims.

We claim:

1. A centrifugal blood pump for pumping blood comprising:

a pump enclosure including a stationary shroud, said shroud having an inlet disposed along a longitudinal axis, and a discharge outlet disposed traverse to said longitudinal axis;

a shaft extending along said longitudinal axis;

an electric motor driving said shaft, said pump enclosure including a motor housing adjacent to and integral with said stationary shroud, said motor being cooled with a fluid contained in a cooling loop in said motor housing, said cooling loop comprising a plurality of bores in a motor rotor disk of said motor, said motor rotor disk comprising a shaft and a hub, and said cooling loop comprising a plurality of bores in said shaft and said hub in said motor rotor disk;

a rotatable impeller having a hub connected to and coaxial with said shaft, said hub having an inlet portion proximate to said inlet said shaft operatively connected to said rotatable impeller, to drive said impeller and force blood from the inlet to the outlet of said pump;

a plurality of curved blades attached to said hub and extending radially outward from said hub, each of said blades having an end proximate to said inlet, said blade ends overlapping at said inlet portion of said hub to present an unbroken span of blade surface area, when viewed in the direction of said axis, and each of said blades having a leading edge adjacent said stationary shroud, facing toward said stationary shroud, and a distal edge opposite to and facing away from said leading edge; and a disc extending radially from said longitudinal axis and connected to said distal edge of said blades, said disc having at least one fluid passageway to allow fluid communication through said disc.

2. The centrifugal blood pump according to claim 1, wherein longitudinal cross-sections of adjacent surfaces of adjacent ones of said blades have a substantially hyperbolic blade profile, and wherein said stationary shroud conforms to the said blade profile, and said leading edges having a curvilinear shape that in a two-dimensional cross-section across the longitudinal axis appear as generally logarithmic spirals.

3. The centrifugal blood pump according to claim 1, wherein said fluid passageway in said disc is a continuous circular slot surrounding said shaft.

4. The centrifugal blood pump according to claim 1, wherein said pump housing further comprises a torus to receive blood discharged by said blades, said torus being continuous and integral with said stationary shroud and of a longitudinal cross-section equal to the diameter of said discharge outlet.

5. The centrifugal blood pump according to claim 4, wherein said torus and said stationary shroud are formed of a plastic material.

6. The centrifugal blood pump according to claim 4, wherein said torus and said stationary shroud are formed of a composite material.

7. The centrifugal blood pump according to claim 1, wherein said pump enclosure is formed of biologically corrosion resistant metal.

8. The centrifugal blood pump according to claim 7, further including a seal stator disposed around said shaft and formed of carbon.

9. The centrifugal blood pump according to claim 7, further including a seal stator disposed around said shaft and formed of composite material.

10. The centrifugal blood pump according to claim 1, wherein said impeller is formed of a plastic material.

11. The centrifugal blood pump according to claim 1, wherein said impeller is formed of a composite material.

12. The centrifugal blood pump according to claim 1, wherein said impeller is formed of a corrosion resistant metal.

13. The centrifugal blood pump according to claim 1, wherein said impeller is formed of gold plated corrosion resistant metal.

14. The centrifugal blood pump according to claim 1, wherein said impeller is formed of gold.

15. The centrifugal blood pump according to claim 1, wherein said impeller is formed of platinum plated corrosion resistant metal.

16. The centrifugal blood pump according to claim 1, wherein said impeller is formed of platinum.

17. The centrifugal blood pump according to claim 1, wherein said impeller is coated with an antithrombogenic coating.

18. The centrifugal blood pump according to claim 1, further comprising a seal stator disposed around said shaft, and wherein the fluid passageway comprises the volume between the impeller and the stationary housing, and is separated from said electric motor with a shaft seal having a seal rotor formed from nitrided titanium.

19. The centrifugal blood pump according to claim 18, further including a seal stator disposed on said shaft and formed from polytetrafluoroethylene.

20. The centrifugal blood pump according to claim 1, wherein said motor is cooled with a fluid contained in said motor housing.

21. The centrifugal blood pump according to claim 20, wherein said fluid is selected from the group consisting of aqueous saline solution, carbon dioxide, helium, and nitrogen.

22. The centrifugal blood pump according to claim 1, wherein at least a portion of said pump is coated with a coating selected from the group consisting of a thermal insulation coating, a tissue biocompatible coating, an antithrombogenic coating, and combinations thereof.

23. The centrifugal blood pump according to claim 1, further comprising a blood pressure transducer for automatic adjustment of the rotational speed responsive to blood pressure sensed by said blood pressure transducer.

24. A centrifugal blood pump for pumping blood comprising:

a pump enclosure including a stationary shroud, said shroud having an inlet disposed along a longitudinal axis, and a discharge outlet disposed traverse to said longitudinal axis;

a shaft extending along said longitudinal axis;

a rotatable impeller having a hub connected to and coaxial with said shaft, said hub having an inlet portion proximate to said inlet said shaft operatively connected to said rotatable impeller, to drive said impeller and force blood from the inlet to the outlet of said pump;

a plurality of curved blades attached to said hub and extending radially outward from said hub, each of said blades having an end proximate to said inlet, said blade ends overlapping at said inlet portion of said hub to present an unbroken span of blade surface area, when viewed in the direction of said axis, and each of said blades having a leading edge adjacent said stationary shroud, facing toward said stationary shroud, and a distal edge opposite to and facing away from said leading edge;

a disc extending radially from said longitudinal axis and connected to said distal edge of said blades, said disc having at least one fluid passageway to allow fluid communication through said disc; and a blood pressure transducer for automatic adjustment of the rotational speed responsive to blood pressure sensed by said blood pressure transducer.

* * * * *